United States Patent
Urade et al.

(10) Patent No.: US 8,865,714 B2
(45) Date of Patent: Oct. 21, 2014

(54) PIPERAZINE COMPOUND CAPABLE OF INHIBITING PROSTAGLANDIN D SYNTHASE

(75) Inventors: Yoshihiro Urade, Suita (JP); Makoto Kitade, Hanno (JP); Kazuhiko Shigeno, Hanno (JP); Keiko Yamane, Hanno (JP); Katsunao Tanaka, Hanno (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 192 days.

(21) Appl. No.: 13/255,134

(22) PCT Filed: Mar. 8, 2010

(86) PCT No.: PCT/JP2010/053760
§ 371 (c)(1),
(2), (4) Date: Sep. 7, 2011

(87) PCT Pub. No.: WO2010/104024
PCT Pub. Date: Sep. 16, 2010

(65) Prior Publication Data
US 2011/0319413 A1    Dec. 29, 2011

(30) Foreign Application Priority Data

Mar. 9, 2009   (JP) .................................. 2009-055721

(51) Int. Cl.
| | | |
|---|---|---|
| *A61K 31/496* | (2006.01) | |
| *A61K 31/5377* | (2006.01) | |
| *C07D 401/12* | (2006.01) | |
| *C07D 403/14* | (2006.01) | |
| *C07D 413/14* | (2006.01) | |
| *C07D 405/12* | (2006.01) | |
| *C07D 413/12* | (2006.01) | |
| *C07D 409/12* | (2006.01) | |
| *C07D 277/82* | (2006.01) | |
| *C07D 207/34* | (2006.01) | |
| *C07D 401/14* | (2006.01) | |
| *C07D 213/81* | (2006.01) | |

(52) U.S. Cl.
CPC ............ *C07D 401/14* (2013.01); *C07D 405/12* (2013.01); *C07D 403/14* (2013.01); *C07D 413/12* (2013.01); *C07D 409/12* (2013.01); *C07D 277/82* (2013.01); *C07D 207/34* (2013.01); *C07D 401/12* (2013.01); *C07D 213/81* (2013.01)
USPC .............. 514/235.8; 514/253.09; 514/254.01; 514/254.05; 544/121; 544/364; 544/366; 544/372

(58) Field of Classification Search
None
See application file for complete search history.

(56) References Cited

U.S. PATENT DOCUMENTS

| | | |
|---|---|---|
| 6,172,113 B1 | 1/2001 | Ohtani |
| 6,384,075 B1 | 5/2002 | Ohtani |
| 6,498,190 B1 | 12/2002 | Ohtani |
| 7,211,672 B2 | 5/2007 | Ghosh |
| 7,504,508 B2 | 3/2009 | Ghosh |
| 7,951,956 B2 | 5/2011 | Urade |
| 2006/0106061 A1 | 5/2006 | Ghosh |
| 2008/0227782 A1 | 9/2008 | Aldous |
| 2009/0156611 A1 | 6/2009 | Oinas |
| 2009/0181966 A1 | 7/2009 | Ghosh |
| 2010/0234377 A1 | 9/2010 | Aicher |
| 2011/0172230 A1 | 7/2011 | Ishii et al. |

FOREIGN PATENT DOCUMENTS

| | | |
|---|---|---|
| JP | 2001288160 A | 10/2001 |
| WO | 9907672 A1 | 2/1999 |
| WO | 2004032848 A2 | 4/2004 |
| WO | 2007007778 A1 | 1/2007 |
| WO | 2007041634 A1 | 4/2007 |
| WO | 2007054623 A2 | 5/2007 |
| WO | 2008/023720 A1 | 2/2008 |
| WO | 2008122787 A1 | 10/2008 |

OTHER PUBLICATIONS

Kajiwara et al. European Journal of Pharmacology vol. 667, pp. 389-395 (2011).*
Joo et al. Mediators of Inflammation vol. 2012, pp. 1-6 (2012).*

(Continued)

*Primary Examiner* — Emily Bernhardt
(74) *Attorney, Agent, or Firm* — Rothwell, Figg, Ernst & Manbeck, P.C.

(57) ABSTRACT

This invention relates to a piperazine compound represented by Formula (I), (I)

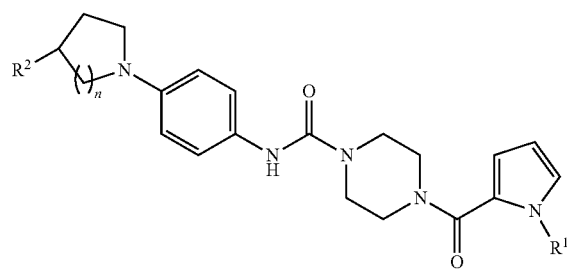

wherein
$R^1$ is $C_{1-6}$ alkyl;
$R^2$ is hydroxy, $C_{1-6}$ alkyl that may have one or more substituents, —(C=O)—N($R^3$)($R^4$), or —(C=O)—$OR^5$;
$R^3$ and $R^4$ are the same or different, and each represents hydrogen or $C_{1-6}$ alkyl that may have one or more substituents, or
$R^3$ and $R^4$, taken together with a nitrogen atom to which $R^3$ and $R^4$ are attached, may form a saturated heterocyclic group;
$R^5$ is hydrogen or $C_{1-6}$ alkyl that may have one or more substituents; and
n is 1 or 2;
or a salt thereof.

6 Claims, No Drawings

(56) References Cited

OTHER PUBLICATIONS

Buyse et al. European Heart Journal, vol. 30, pp. 116-124 (2009).*

Hardy et al., "The Bronchoconstrictor Effect of Inhaled Prostaglandin D2 in Normal and Asthmatic Men", The New England Journal of Medicine, vol. 311, 1984, No. 4, pp. 209-213.

Hyo et al., "Expression of Prostaglandin D2 Synthase in Activated Eosinophils in NasalPolyps", Arch Otolaryngol Head Neck Surg, vol. 133, No. 7, 2007, pp. 693-700.

Lewis et al., Prostaglandin D2 Generation after Activation of Rat and Human Mast Cells with ANTI-IgE, The Journal of Immunology, vol. 129, No. 4, 1982, pp. 1627-1631.

Murray et al., "Release of Prostaglandin D2 into Human Airways during Acute Antigen Challenge", The New England Journal of Medicine, vol. 315, 1986, pp. 800-804.

Mohri et al., "Inhibition of Prostaglandin D Synthase Suppresses Muscular Necrosis", The American Journal of Pathology, vol. 174, No. 5, 2009, pp. 1735-1744.

Okinaga et al., "Induction of hematopoietic prostaglandin D synthase in hyalinated necrotic muscle fibers: its implication in grouped necrosis", Acta Neuropathol (2002), 104, pp. 377-384.

\* cited by examiner

PIPERAZINE COMPOUND CAPABLE OF INHIBITING PROSTAGLANDIN D SYNTHASE

CROSS REFERENCE TO RELATED APPLICATION

This application is a 35 U.S.C. 371 National Phase Entry Application from PCT/JP2010/053760, filed Mar. 8, 2010, which claims the benefit of Japanese Patent Application No. 2009-055721 filed on Mar. 9, 2009, the disclosure of which is incorporated herein in its entirety by reference.

TECHNICAL FIELD

The present invention relates to a piperazine compound or a salt thereof, and a pharmaceutical composition containing the piperazine compound or salt thereof as an active ingredient, and in particular, to an agent for preventing and/or treating allergic disease, inflammatory disease, and myodegenerative disease due to its hematopoietic prostaglandin D synthase inhibiting action.

BACKGROUND ART

Prostaglandin D2 (PGD2) is the inflammatory mediator produced and released in the largest amounts by mast cells activated by the binding of antigens with immunoglobulin E (NPL 1), and is considered to play an important role in the elucidation of allergic reactions. PGD2 is detected at high concentration in an asthmatic's bronchioalveolar fluid (NPL 2), and it was reported that bronchoconstriction was induced by prostaglandin D2 inhalation in asthmatic patients but not healthy subjects (NPL 3).

On the other hand, synthases that generate PGD2 are referred to as prostaglandin D synthases. Two different types, hematopoietic prostaglandin D synthase and lipocalin-type prostaglandin D synthase, are known to exist. PGD2 participates in the onset and exacerbation of various diseases, including allergies, and in the regulatory mechanisms of the body; therefore, pharmaceutical preparations that can ameliorate excess production are considered to be very effective in the treatment of various diseases.

Human hematopoietic prostaglandin D synthases (H-PGDS) are mainly distributed throughout the placenta, lung, fetus liver, lymph node, brain, heart, thymus, bone marrow, and spleen. Moreover, at the cellular level, they are reported to be expressed in microglia in the brain, megakaryocyte, and Langerhans cells in the skin; Kupffer cells in the liver; macrophages; and many antigen-presenting cells such as dendritic cells, mast cells, and Th2 cells.

Moreover, from the fact that H-PGDS are highly expressed in mast cells or inflammatory cells at nasal mucosa in allergic rhinitis, or nasal polyps in chronic sinusitis, it is thought that PGD2 produced by H-PGDS plays an important role in the onset and exacerbation of allergic diseases, such as asthma, rhinosinusitis, dermatitis, and chronic obstructive pulmonary disease (NPL4). Further, the expression of H-PGDS is confirmed in the necrosed part of skeletal muscle, in which the expression of H-PGDS does not generally occur (NPL5). For this reason, it is suggested that PGD2 produced by a hematopoietic prostaglandin D synthase participates in diseases accompanied by tissue damage, such as muscular dystrophy, amyotrophic lateral sclerosis, multiple sclerosis, ulcerative colitis, rheumatoid arthritis, and chronic obstructive arterial disease (NPL6).

Therefore, an H-PGDS inhibitor is expected to find application as a pharmaceutical preparation that is useful as an agent for preventing and/or treating diseases such as allergic disease and inflammatory disease in which PGD2 produced by a hematopoietic prostaglandin D synthase or metabolite thereof participates, and muscle necrosis and traumatic brain injury.

There are some reports on an H-PGDS inhibitor (for example, PTL 1 and 2), and Patent Literature 3 discloses an H-PGDS inhibitor having a structure similar to that of the compound of the present invention. In addition, piperazine compounds have been widely studied as useful pharmacological agents in addition to H-PGDS inhibitors.

Patent Literature 4 discloses as a hedgehog signaling inhibitor, a piperazine compound having a furyl carbonyl piperazine structure. Patent Literature 5 discloses a wide range of piperazine compounds as compounds that interact with potassium channels.

Patent Literature 6 discloses a urea compound having a piperazine ring as a compound useful for treating a disease in which fatty acid amide hydrolase participates.

CITATION LIST

Patent Literature

PTL 1: WO2007-007778
PTL 2: WO2007-041634
PTL 3: WO2008-122787
PTL 4: WO2007-054623
PTL 5: WO99/007672
PTL 6: WO2008-023720

Non-Patent Literature

NPL 1: J. Immunol., 129, 1627-1631 (1982)
NPL 2: N. Eng. J. Med., 315, 800-804 (1986)
NPL 3: N. Eng. J. Med., 311, 209-213 (1984)
NPL 4: Arch. Otolaryngol Head Neck Surg., 133, 693-700 (2007)
NPL 5: Acta Neuropathol., 104, 377-384 (2002)
NPL 6: Am J Pathol., 174(5), 1735-1744 (2009)

SUMMARY OF INVENTION

Technical Problem

The main object of the present invention is to provide a novel compound that exhibits, at a low dose, a high inhibitory effect on prostaglandin D synthases, and in particular, on H-PGDS.

Another ancillary object of the present invention is to provide a medicine with few side effects and high safety, the medicine being effective, due to its H-PGDS inhibiting action, in preventing and/or treating diseases mediated by PGD2, which is generated by a synthase or metabolite thereof.

Solution to Problem

The present inventors conducted extensive research on compounds having an H-PGDS inhibiting action, and found that a novel piperazine compound represented by Formula (I) has an extremely excellent inhibiting action on H-PGDS. The inventors conducted further research and have accomplished the present invention.

The present invention provides a piperazine compound, a pharmaceutical composition, a prostaglandin D synthase inhibitor, and an agent for preventing and/or treating a disease in which prostaglandin D2 or a metabolite thereof participates as described below.

1. A piperazine compound represented by Formula (I),

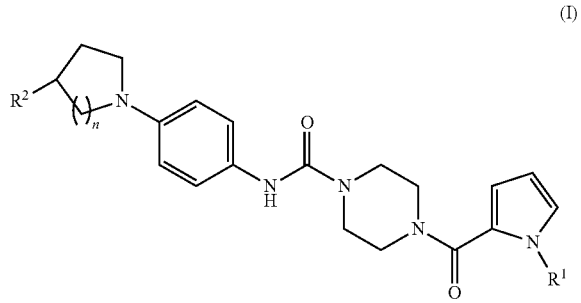

wherein
R$^1$ is C$_{1-6}$ alkyl;
R$^2$ is hydroxy, C$_{1-6}$ alkyl that may have one or more substituents, —(C=O)—N(R$^2$)(R$^4$), or —(C=O)—OR$^5$;
R$^3$ and R$^4$ are the same or different, and each represents hydrogen or C$_{1-6}$ alkyl that may have one or more substituents, or
R$^3$ and R$^4$, taken together with a nitrogen atom to which R$^3$ and R$^4$ are attached, may form a saturated heterocyclic group;
R$^5$ is hydrogen or C$_{1-6}$ alkyl that may have one or more substituents; and
n is 1 or 2;
or a salt thereof.

2. The piperazine compound or salt thereof according to Item 1, wherein
R$^1$ is methyl or ethyl;
R$^2$ is hydroxy, C$_{1-6}$ alkyl that may have one or more saturated or unsaturated heterocyclic groups as substituents, —(C=O)—N(R$^3$)(R$^4$), or —(C=O)—OR$^5$;
R$^3$ and R$^4$ are the same or different, and each represents hydrogen or C$_{1-6}$ alkyl that may have one or more saturated or unsaturated heterocyclic groups as substituents, or
R$^3$ and R$^4$, taken together with a nitrogen atom to which R$^3$ and R$^4$ are attached, may form pyrrolidinyl, piperidinyl, piperazinyl, and morpholino;
R$^5$ represents hydrogen, methyl, ethyl, tert-butyl, or benzyl; and
n is 1 or 2.

3. The piperazine compound or salt thereof according to Item 1 or 2, wherein
R$^1$ is methyl;
R$^2$ is C$_{1-3}$ alkyl that may have morpholino, pyrazolyl, or triazolyl as a substituent, —(C=O)—N(R$^3$)(R$^4$), or —(C=O)—OR$^5$; and the triazolyl may have one or two substituents;
R$^3$ and R$^4$, taken together with a nitrogen atom to which R$^3$ and R$^4$ are attached, may form morpholino;
R$^5$ represents hydrogen, methyl, or ethyl; and
n is 2.

4. The piperazine compound or salt thereof according to any one of Items 1 to 3, wherein
R$^1$ is methyl;
R$^2$ is straight C$_{1-3}$ alkyl that may have any one of 1,2,3-triazolyl, 3,5-dimethyl-1,2,4-triazolyl, and morpholino as a substituent, —(C=O)—N(R$^3$)(R$^4$), or —(C=O)—OR$^5$;
R$^3$ and R$^4$, taken together with a nitrogen atom to which R$^3$ and R$^4$ are attached, may form morpholino;
R$^5$ represents hydrogen or ethyl; and
n is 2.

5. The piperazine compound or salt thereof according to Item 1 selected from the group consisting of:
N-(4-(4-hydroxypiperidin-1-yl)-phenyl)-4-((1-methylpyrrol-2-yl)-carbonyl)-1-piperazinecarboxamide,
4-((((1-methylpyrrol-2-yl)-carbonyl)-1-piperazinyl)carbonyl)amino-4-phenylpiperidine-4-carboxylic acid,
4-((1-methylpyrrol-2-yl)-carbonyl)-N-(4-(4-morpholin-1-yl-carbonylpiperidin-1-yl)-phenyl)-1-piperazinecarboxamide,
4-((1-methylpyrrol-2-yl)-carbonyl)-N-(4-(4-morpholinomethylpiperidin-1-yl)-phenyl)-1-piperazinecarboxamide,
4-((1-methylpyrrol-2-yl)-carbonyl)-N-(4-(3-(2-(1,2,4-triazole-1-yl)-ethyl)pyrrolidin-1-yl)-phenyl)-1-piperazinecarboxamide,
4-((1-methylpyrrol-2-yl)-carbonyl)-N-(4-(4-morpholinoethylpiperidin-1-yl)-phenyl)-1-piperazinecarboxamide,
4-(1-methylpyrrol-2-yl)-carbonyl)-N-(4-(4-(2-(1,2,3-triazol-1-yl)-ethyl)piperidin-1-yl)-phenyl)-1-piperazinecarboxamide,
4-((1-methylpyrrol-2-yl)-carbonyl)-N-(4-(4-(2-(1,2,4-triazol-1-yl)-ethyl)piperidin-1-yl)-phenyl)-1-piperazinecarboxamide,
4-((1-methylpyrrol-2-yl)-carbonyl)-N-(4-(4-(2-(3,5-dimethyl-1,2,4-triazol-1-yl)-ethyl)piperidin-1-yl)-phenyl)-1-piperazinecarboxamide,
4-((1-methylpyrrol-2-yl)-carbonyl)-N-(4-(4-(2-(pyrazol-1-yl)-ethyl)piperidin-1-yl)-phenyl)-1-piperazinecarboxamide,
4-((1-methylpyrrol-2-yl)-carbonyl)-N-(4-(4-(3-(1,2,4-triazol-1-yl)-propyl)piperidin-1-yl)-phenyl)-1-piperazinecarboxamide,
4-((1-methylpyrrol-2-yl)-carbonyl)-N-(4-(4-(3-(1,2,3-triazol-1-yl)-propyl)piperidin-1-yl)-phenyl)-1-piperazinecarboxamide,
4-((1-ethylpyrrol-2-yl)-carbonyl)-N-(4-(4-morpholin-1-yl-carbonylpiperidin-1-yl)-phenyl)-1-piperazinecarboxamide,
4-((1-methylpyrrol-2-yl)-carbonyl)-N-(4-(4-piperidin-1-yl-carbonylpiperidin-1-yl)-phenyl)-1-piperazinecarboxamide,
4-((1-methylpyrrol-2-yl)-carbonyl)-N-(4-(4-(4-methylpiperazin-1-yl-carbonyl)piperidin-1-yl)-phenyl)-1-piperazinecarboxamide,
4-((1-methylpyrrol-2-yl)-carbonyl)-N-(4-(4-(2-morpholinoethylcarbamoyl)piperidin-1-yl)-phenyl)-1-piperazinecarboxamide, and
4-((1-methylpyrrol-2-yl)-carbonyl)-N-(4-(4-(pyridin-3-ylmethylcarbamoyl)piperidin-1-yl)-phenyl)-1-piperazinecarboxamide.

6. A pharmaceutical composition comprising an effective amount of at least one of the compounds according to Items 1 to 5 or pharmaceutically acceptable salts thereof, and a pharmaceutically acceptable carrier.

7. A prostaglandin D synthase inhibitor comprising an effective amount of a compound according to any one of Items 1 to 5 or a pharmaceutically acceptable salt thereof, and a pharmaceutically acceptable carrier.

8. An agent for preventing and/or treating a disease in which prostaglandin D2 or a metabolite thereof participates, the agent comprising an effective amount of a compound according to any one of Items 1 to 5 or a pharmaceutically acceptable salt thereof, and a pharmaceutically acceptable carrier.

9. The agent according to Item 8, wherein the disease in which prostaglandin D2 or a metabolite thereof participates is an allergic disease, inflammatory disease, or myodegenerative disease.

10. A method for preventing and/or treating a disease in which prostaglandin D2 or a metabolite thereof participates, the method comprising administering, to a mammal, a compound according to any one of Items 1 to 5 in an amount effective for preventing or treating the disease.

11. Use of a compound according to any one of Items 1 to 5 for producing an agent for preventing and/or treating a disease in which prostaglandin D2 or a metabolite thereof participates.

12. The compound according to any one of Items 1 to 5 for use in a method for preventing and/or treating a disease in which prostaglandin D2 or a metabolite thereof participates.

Advantageous Effects of Invention

The present invention provides a novel piperazine compound represented by the above Formula (I) or a salt thereof, which is useful as a prostaglandin D synthase inhibitor, and in particular an H-PGDS inhibitor.

The piperazine compound or a salt thereof according to the present invention has excellent H-PGDS inhibitory activity in vitro. Further, since guinea pigs with antigen-induced rhinitis show H-PGDS production inhibiting action in a nasal cavity washing liquid and eosinophilic infiltration inhibiting action, it is revealed that the piperazine compound or a salt thereof has an excellent nasal congestion improving action and eosinophilic inflammation inhibiting action. Further, in a forelimb grip strength test using mdx mice, loss in muscle strength is remarkably improved, which indicates that the piperazine compound or a salt thereof of the present invention is useful for treating myodegenerative disease, such as muscular dystrophy.

Thus, based on its excellent H-PGDS inhibitory activity, the piperazine compound or a salt thereof according to the present invention is useful as an agent for preventing and/or treating a disease in which PGD2 or a metabolite thereof participates, such as an allergic disease, inflammatory disease, and myodegenerative disease, and is expected to have other useful effects.

DESCRIPTION OF EMBODIMENTS

A piperazine compound represented by Formula (I),

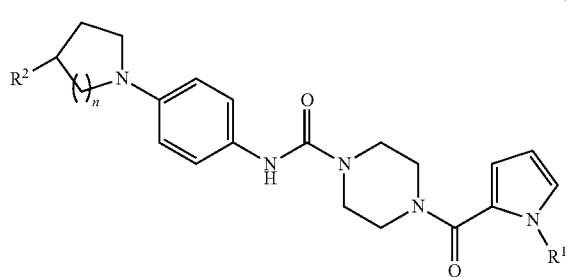

(I)

wherein
$R^1$ is $C_{1-6}$ alkyl;
$R^2$ is hydroxy, $C_{1-6}$ alkyl that may have one or more substituents, —(C=O)—N($R^3$)($R^4$), or —(C=O)—$OR^5$;
$R^3$ and $R^4$ are the same or different, and each represents hydrogen or $C_{1-6}$ alkyl that may have one or more substituents, or $R^3$ and $R^4$, taken together with a nitrogen atom to which $R^3$ and $R^4$ are attached, may form a saturated heterocyclic group;
$R^5$ is hydrogen or $C_{1-6}$ alkyl that may have one or more substituents; and
n is 1 or 2;
or a salt thereof.

The piperazine compound of the present invention, which is represented by Formula (I), is a compound having both (N-alkyl pyrrol-2-yl)carbonyl and phenylaminocarbonyl, and is a novel compound not specifically disclosed in the aforementioned literature.

For example, Patent Literature 3 (WO2008/122787) discloses a wide range of piperazine compounds that inhibit H-PGDS; however, it is completely silent about a piperazine compound having (N-alkylpyrrol-2-yl)carbonyl, which is contained in the compound of the present invention. Further, as shown in the Test Examples described below, the compounds demonstrated in the Examples (Reference Examples 13 to 18) of Patent Literature 3 do not exhibit PGD2 production inhibiting action in a nasal cavity washing liquid in guinea pigs with antigen-induced rhinitis.

Patent Literature 4 (WO2007/054623) discloses as an inhibitor of hedgehog signaling a piperazine compound having a furyl carbonyl piperazine structure; however, Patent Literature 4 is different from the present invention in that (N-alkylpyrrol-2-yl)carbonyl used in the compound of the present invention is limited to furyl carbonyl. Further, Patent Literature 4 is completely silent about H-PGDS inhibiting action.

Patent Literature 5 (WO99/007672) discloses a furyl carbonyl piperazine compound, a benzoylpiperazine compound, etc., as a compound that interacts with a potassium channel. However, Patent Literature 5 does not disclose a compound having (N-alkylpyrrol-2-yl)carbonyl as in the present compound, and is completely silent about H-PGDS inhibiting action.

Patent Literature 6 (WO2008/023720) discloses as a compound useful for treating disease associated with fatty acid amide hydrolase a urea compound having a piperidine ring. However, Patent Literature 6 does not disclose a compound having (N-alkylpyrrol-2-yl)carbonyl as in the present compound, and is completely silent about H-PGDS inhibiting action.

As shown in the Test Examples below, a piperazine compound having no (N-alkylpyrrol-2-yl)carbonyl exhibits almost no H-PGDS inhibiting action.

Examples of "substituents" in the present specification include halogen, hydroxy, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxy, alkoxycarbonyl, aralkyloxycarbonyl, carbamoyl, saturated or unsaturated heterocyclic groups, aromatic hydrocarbon, saturated heterocycloxy group, etc. When such a substituent is present, the number thereof is typically 1 to 3.

In the substituents, examples of halogen include chlorine, bromine, fluorine, and iodine.

In the substituents, alkyl or halogenoalkyl is preferably a straight or branched $C_{1-6}$ alkyl group or a group in which one to all of the hydrogen atoms of the alkyl group is substituted with halogen described above. Examples thereof include alkyl groups such as methyl, ethyl, n-propyl, isopropyl, n-butyl, isobutyl, sec-butyl, tert-butyl, pentyl, and hexyl, and halogeno alkyl groups such as trifluoromethyl.

In the substituents, cycloalkyl is preferably a $C_{3-7}$ cycloalkyl group, and examples thereof include cyclopropyl, cyclobutyl, cyclopentyl, cyclohexyl, and cycloheptyl.

In the substituents, cycloalkyl-alkyl is preferably a $C_{1-6}$ alkyl group substituted with $C_{3-7}$ cycloalkyl, and examples thereof include cyclopropylmethyl, cyclopropylethyl, cyclobutylmethyl, cyclopentylmethyl, and cyclohexylmethyl.

In the substituents, aralkyl is preferably a straight or branched $C_{1-6}$ alkyl group substituted with a $C_{6-14}$ aromatic hydrocarbon group, and examples thereof include benzyl, phenylethyl, phenylpropyl, naphthylmethyl, and naphthylethyl.

In the substituents, alkenyl is preferably a $C_{2-6}$ alkenyl group containing a carbon-carbon double bond, and examples thereof include vinyl, allyl, methylvinyl, propenyl, butenyl, pentenyl, and hexenyl.

In the substituents, alkynyl is preferably a $C_{2-6}$ alkynyl group containing a carbon-carbon triple bond, and examples thereof include ethynyl and propargyl.

In the substituents, alkoxy or halogenoalkoxy is preferably a straight or branched $C_{1-6}$ alkoxy group or the alkoxy group substituted with halogen described above, and examples thereof include methoxy, ethoxy, n-propoxy, isopropoxy, 1-methylpropoxy, n-butoxy, isobutoxy, tert-butoxy, 2-methylbutoxy, neopentyloxy, pentan-2-yloxy, fluoromethoxy, difluoromethoxy, trifluoromethoxy, 1,1-difluoroethoxy, 2,2-difluoroethoxy, 2,2,2-trifluoroethoxy, 1,1,2,2-tetrafluoroethoxy, perfluoroethoxy, 3-fluoro-2-(fluoromethyl)-propoxy, 1,3-difluoropropan-2-yloxy, and 2,2,3,3,3-pentafluoro-1-propoxy.

In the substituents, cycloalkoxy is preferably a $C_{3-7}$ cycloalkoxy group, and examples thereof include cyclopropoxy, cyclobutoxy, cyclopenthyloxy, cyclohexyloxy, and cycloheptyloxy.

In the substituents, cycloalkyl-alkoxy is preferably a $C_{1-6}$ alkoxy group substituted with $C_{3-7}$ cycloalkyl, and examples thereof include cyclopropylmethoxy, cyclopropylethoxy, cyclobutylmethoxy, cyclopentylmethoxy, and cyclohexylmethoxy.

In the substituents, alkylthio is preferably a straight or branched $C_{1-6}$ alkylthio group, and examples thereof include methylthio, ethylthio, n-propylthio, isopropylthio, n-butylthio, isobutylthio, sec-butylthio, tert-butylthio, pentylthio, and hexylthio.

In the substituents, cycloalkyl-alkylthio is preferably a $C_{1-6}$ alkylthio group substituted with $C_{3-7}$ cycloalkyl, and examples thereof include cyclopropylmethylthio, cyclopropylethylthio, cyclobutylmethylthio, cyclopentylmethylthio, and cyclohexylmethylthio.

In the substituents, aralkyloxy is preferably an oxy group having the aforementioned aralkyl group, and examples thereof include benzyloxy, phenethyloxy, phenylpropyloxy, naphthylmethyloxy, and naphthylethyloxy.

In the substituents, mono- or di-alkylamino is an amino group mono- or di-substituted with a straight or branched $C_{1-6}$ alkyl group, and examples thereof include methylamino, dimethylamino, ethylamino, diethylamino, and methylethylamino.

In the substituents, cycloalkyl-alkylamino is an alkylamino group substituted with the aforementioned cycloalkyl group, and examples thereof include cyclopropylmethylamino, cyclobutylmethylamino, and cyclopentylmethylamino.

In the substituents, acyl is a straight or branched $C_{1-6}$ acyl group or benzoyl group, and examples thereof include formyl, acetyl, propionyl, n-butyryl, isobutyryl, valeryl, isovaleryl, and pivaloyl.

In the substituents, acyloxy is a straight or branched $C_{1-6}$ acyloxy group or benzoyloxy group, and examples thereof include formyloxy, acetoxy, propionyloxy, n-butyryloxy, isobutyryloxy, valeryloxy, isovaleryloxy, and pivaloyloxy.

In the substituents, alkoxycarbonyl is a carbonyl group substituted with the aforementioned alkoxy group, and examples thereof include methoxycarbonyl, ethoxycarbonyl, n-propoxycarbonyl, isopropoxycarbonyl, 1-methylpropoxycarbonyl, n-butoxycarbonyl, isobutoxycarbonyl, tert-butoxycarbonyl, 2-methyl-butoxycarbonyl, neopentyloxycarbonyl, and pentan-2-yloxycarbonyl.

In the substituents, aralkyloxycarbonyl is preferably a carbonyl group substituted with the aforementioned aralkyloxy group, and examples thereof include benzyloxycarbonyl, phenethyloxycarbonyl, phenylpropyloxycarbonyl, naphthlmethyloxycarbonyl, and naphthylethyloxycarbonyl.

In the substituents, examples of carbamoyl include —CONH2, (mono- or di-alkyl)carbamoyl, (mono- or di-aryl)carbamoyl, (N-alkyl-N-aryl)carbamoyl, pyrrolidinocarbamoyl, piperidinocarbamoyl, piperazinocarbamoyl, and morpholinocarbamoyl.

In the substituents, saturated or unsaturated heterocyclic groups are preferably monocyclic or bicyclic saturated or unsaturated heterocyclic groups that may have any one of oxygen, nitrogen, or sulfur, preferably in an amount of 1 to 4. Examples thereof include pyrrolidinyl, piperidinyl, piperazinyl, hexamethyleneimino, morpholino, thiomorpholino, homopiperazinyl, tetrahydrofuranyl, tetrahydropyranyl, imidazolyl, thienyl, furyl, pyrrolyl, oxazolyl, isoxazolyl, thiazolyl, isothiazolyl, pyrazolyl, triazolyl, tetrazolyl, pyridyl, pyrazyl, pyrimidinyl, pyridazinyl, indolyl, isoindolyl, indazolyl, methylenedioxyphenyl, ethylenedioxyphenyl, benzofuranyl, dihydrobenzofuranyl, benzoimidazolyl, benzoxazolyl, benzothiazolyl, purinyl, quinolyl, isoquinolyl, quinazolinyl, and quinoxalyl.

In the substituents, aromatic hydrocarbon is preferably a $C_{6-14}$ aromatic hydrocarbon group, and examples thereof include phenyl and naphthyl.

In the substituents, saturated heterocycloxy group is a monocyclic saturated heterocyclic group having any one of oxygen, nitrogen, and sulfur in an amount of one or two, and examples thereof include oxy groups having pyrrolidinyl, piperidinyl, piperazinyl, hexamethyleneimino, morpholino, thiomorpholino, or homopiperazinyl, such as tetrahydrofuranyloxy and tetrahydropyranyloxy.

"$C_{1-6}$ alkyl" represented by $R^1$ in Formula (I) is a straight- or branched-$C_{1-6}$ alkyl group, and examples thereof include methyl, ethyl, n-propyl, isopropyl, n-butyl, isobutyl, tert-butyl, n-pentyl, and n-hexyl. Of these, methyl and ethyl are preferable, and methyl is more preferable.

Examples of the "$C_{1-6}$ alkyl" of the "$C_{1-6}$ alkyl that may have one or more substituents" represented by $R^2$ in Formula (I) include $C_{1-6}$ alkyl represented by $R^1$ in Formula (I). Of these, $C_{1-3}$ alkyl is preferable, and straight $C_{1-3}$ alkyl such as methyl, ethyl, and n-propyl are more preferable.

Examples of the "substituents" of the "$C_{1-6}$ alkyl that may have one or more substituents" represented by $R^2$ include the above-mentioned substituents. Hydroxy, and saturated or unsaturated heterocyclic groups are preferable; morpholino, pyrazolyl, and triazolyl are more preferable; and morpholino, 1,2,3-triazolyl, and 1,2,4-triazolyly are particularly preferable. The unsaturated heterocyclic groups may have substituents. A preferable substituent is methyl, and the number of substituents is 1 or 2. Preferable examples of "$C_{1-6}$ alkyl that may have one or more substituents" represented by $R^2$ include morpholino, 1,2,3-triazolyl, and 3,5-dimethyl-1,2,4-triazolyl.

Examples of the "$C_{1-6}$ alkyl" of the "$C_{1-6}$ alkyl that may have one or more substituents" represented by $R^3$ and $R^4$ in Formula (I) include $C_{1-6}$ alkyl represented by $R^1$ in Formula (I). Of these, $C_{1-3}$ alkyl is preferable.

Examples of the "substituents" of the "$C_{1-6}$ alkyl that may have one or more substituents" represented by $R^3$ and $R^4$ include the above-mentioned substituents. Of these, saturated or unsaturated heterocyclic groups are preferable.

Examples of "saturated heterocyclic groups" that may be formed by $R^3$ and $R^4$ in Formula (I) together with a nitrogen atom to which $R^3$ and $R^4$ are attached, include pyrrolidinyl, piperidinyl, piperazinyl, and morpholino, and morpholino is preferable.

Preferable examples of the "$C_{1-6}$ alkyl that may have one or more substituents" represented by $R^5$ in Formula (I) include methyl, ethyl, tert-butyl, and benzyl.

In Formula (I), n represents 1 or 2, and preferably 2.

The piperazine compound of the present invention can be produced according to the following Reaction Schemes 1 to 5.

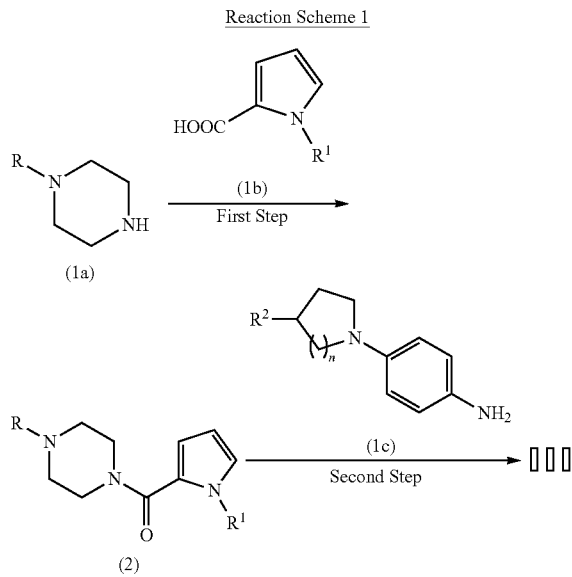

Reaction Scheme 1

(1a) + (1b) → First Step → (2) + (1c) → Second Step → (I)

In the above Reaction Scheme 1, $R^1$ and $R^2$ are the same as above, R represents a protective group of amino group or hydrogen, and n represents 1 or 2.

The method of the present invention comprises a first step in which a piperazine compound shown in Formula (1a) or a salt thereof is condensed with a pyrrolecarboxylic acid compound shown in Formula (1b) or an active species thereof by an ordinary method to form an amide compound shown in Formula (2), and a second step in which an amine compound obtained by deprotecting a protective group of amino group or a salt thereof is condensed with an amine compound shown in Formula (1c) or an active species thereof by an ordinary method to form a compound shown in Formula (I).

First Step

In the first step, the piperazine compound shown in Formula (1a) or a salt thereof is condensed with the pyrrolecarboxylic acid compound shown in Formula (1b) or an active species thereof by an ordinary method, thereby forming the amide compound shown in Formula (2).

Examples of the active species of compound (1b) include active esters, e.g., ordinary esters such as methyl esters; acid halides such as acid chlorides; and N-hydroxybenzotriazole; and symmetrical acid anhydrides; and mixed acid anhydrides with alkyl carbonic acids.

When the compound (1b) is reacted with a free acid, or when an active ester or acid halide is reacted without being isolated, a condensation agent such as 1-ethyl-3-(3-dimethylamino propyl)carbodiimide hydrochloride and 4-(4,6-dimethoxy-1,3,5-triazin-2-yl)-4-methylmorpholinium chloride may be used.

When 0.5 to 10 moles, and preferably 0.8 to 2 moles of the carboxylic acid compound shown in Formula (1b) or an active species thereof is used relative to 1 mole of the piperazine compound shown in Formula (1a) or a salt thereof, the amount of the condensation is 0.5 to 20 moles, and preferably 0.8 to 3 moles relative to 1 mole of the piperazine compound shown in Formula (1a) or a salt thereof.

Although dependent on the active species or condensation agent used, the reaction is normally carried out in a solvent which is inactive to the reaction at −20 to 150° C., and preferably at 0 to 100° C. Examples of such a solvent include a halogenated hydrocarbon such as dichloromethane and chloroform; an aromatic hydrocarbon such as toluene; an ether such as tetrahydrofuran; an ester such as ethyl acetate; an alcohol such as methanol and ethanol; water; acetonitrile; N,N-dimethylformamide; N,N-dimethylacetamide; dimethylsulfoxide; and pyridine.

The reaction may proceed smoothly if it is carried out in the presence of about 0.5 to 20 moles, and preferably 0.8 to 5 moles of a base such as triethylamine, diisopropylethylamine, N-methylmorpholine, N,N-diethylaniline, 4-(N,N-dimethylamino)pyridine, and pyridine, relative to 1 mole of the piperazine compound shown in Formula (1a) or a salt thereof.

Second Step

In the second step, the protective group R of amino group in the amide compound shown in Formula (2) is deprotected by an ordinary, known method, and the result and the amine compound shown in Formula (1c) or an active species thereof are condensed by an ordinary method to form the compound shown in Formula (I).

Deprotection can be carried out under acidic conditions when the protective group R is formyl or tert-butoxycarbonyl, and deprotection can be performed by a catalytic reduction method when the protective group R is benzyl or benzyloxycarbonyl.

In the condensation, it is preferable to use an active species having an elimination group that is prepared by reacting the amine compound shown in Formula (1c) with triphosgene, 1,1'-carbonyldiimidazole (CDI), phenyl chloroformate, 4-nitrophenyl chloroformate, ethyl chloroformate, or the like, in a solvent that is inactive to the reaction, such as dichloromethane, tetrahydrofuran, acetonitrile, ethyl acetate, or N,N-dimethylacetamide, at −20 to 150° C., and preferably 0 to 100° C., in the presence or absence of an organic base such as triethylamine or pyridine.

The active species of Formula (1c) may have an elimination group. The active species may be used for reaction after isolation or may be prepared in a reaction system and used without isolation. Examples of the elimination group include chlorine, imidazolyl, phenoxy, 4-nitrophenoxy, and ethoxy.

Examples of the salts of the amine compound shown in Formula (2) include acid addition salts with inorganic acids, such as hydrochloric acid, hydrobromic acid, and sulfuric acid, or with organic acids, such as carbonic acid and methanesulfonic acid.

When 0.5 to 10 moles, and preferably 0.8 to 2 moles, of the amine compound shown in Formula (3) or a salt thereof is used relative to 1 mole of the amine compound shown in Formula (1c) or an active species thereof, the amount of the condensation is 0.5 to 20 moles, and preferably 0.8 to 3 moles, relative to 1 mole of the amine compound shown in Formula (1c) or a salt thereof.

Although dependent on the active species or condensation agent used, the reaction is normally carried out in a solvent that is inactive to the reaction at −20 to 150° C., and preferably at 0 to 100° C. Examples of the solvent include a halogenated hydrocarbon such as dichloromethane and chloroform; an aromatic hydrocarbon such as toluene; an ether such as tetrahydrofuran; an ester such as ethyl acetate; an alcohol such as methanol and ethanol; water; acetonitrile; N,N-dimethylformamide; N,N-dimethylacetamide; dimethylsulfoxide; and pyridine.

The reaction may proceed smoothly if it is carried out in the presence of about 0.5 to 20 moles, and preferably 0.8 to 5 moles, of a base such as triethylamine, diisopropylethylamine, N-methylmorpholine, N,N-diethylaniline, 4-(N,N-dimethylamino)pyridine, and pyridine, relative to 1 mole of the amine compound shown in Formula (1c) or an active species thereof.

The compound (I) of the present invention can be obtained by performing the first step and the second step.

The piperazine compound shown in Formula (1a) or a salt thereof, the pyrrolecarboxylic acid compound shown in Formula (1b) or an active species thereof, and the amine compound shown in Formula (1c) or a salt thereof are known in the art, or can be manufactured in accordance with a method known in the art.

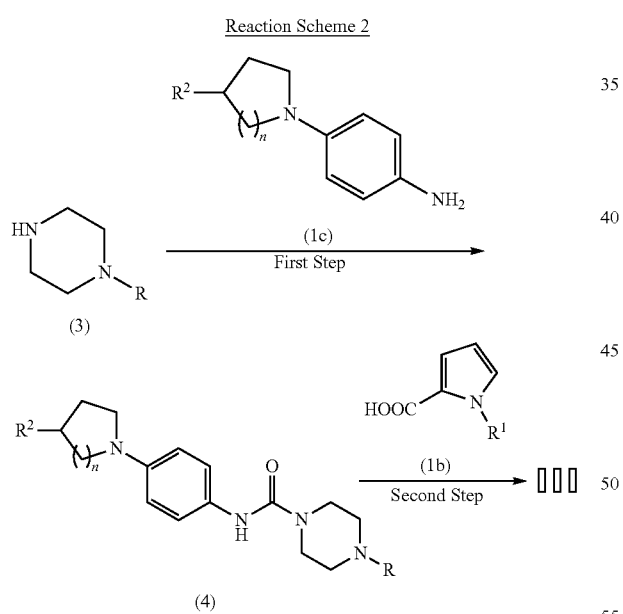

In the above Reaction Scheme 2, $R^1$ and $R^2$ are as defined above, R is a protective group of amino group or hydrogen, and n is 1 or 2.

The method of the present invention comprises a first step in which a piperazine compound shown in Formula (3) or a salt thereof is condensed with an amine compound shown in Formula (1c) or an active species thereof by an ordinary method to form a urea compound shown in Formula (4), and a second step in which an amine compound obtained by deprotecting a protective group of amino group or a salt thereof is condensed with a pyrrolecarboxylic acid compound shown in Formula (1b) or an active species thereof by an ordinary method to form a compound shown in Formula (I).

First Step

In the first step, the piperazine compound shown in Formula (3) and a salt thereof are condensed with the amine compound shown in Formula (1c) according to an ordinary method as in the condensation reaction performed in the second step of Reaction Scheme 1, thereby obtaining the urea compound shown in Formula (4).

Second Step

In the second step, the protective group R of amino group in the urea compound shown in Formula (4) is deprotected, as in the deprotection reaction performed in the second step of Reaction Scheme 1, and then the pyrrolecarboxylic acid compound shown in Formula (1b) or an active species thereof is condensed by an ordinary method, as in the first step of Reaction Scheme 1, thereby obtaining the compound shown in Formula (I).

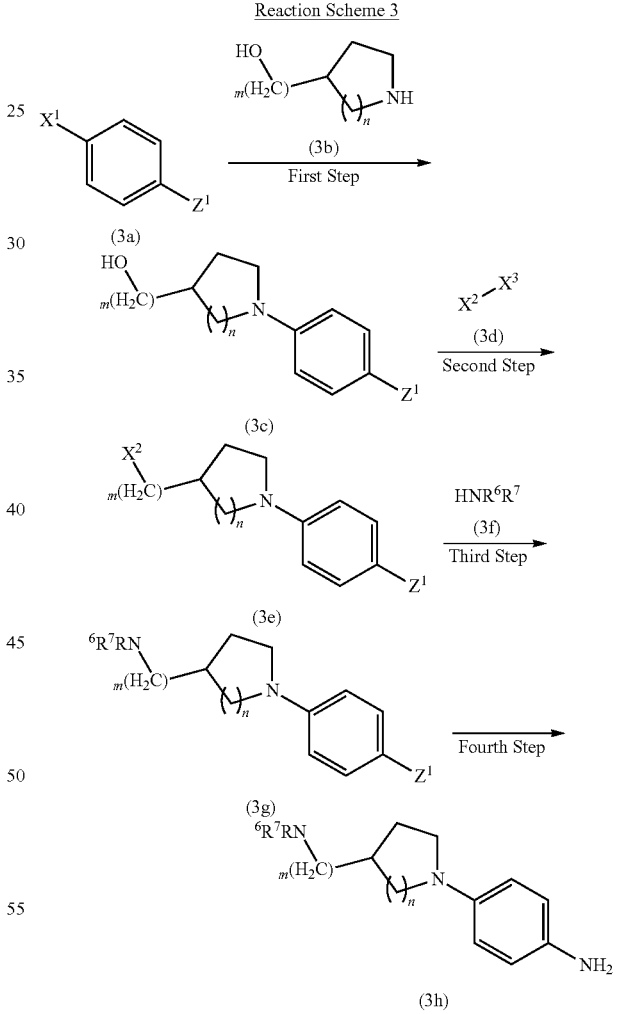

In the above Reaction Scheme 3, $X^1$, $X^2$, and $X^3$ are each an elimination functional group, $Z^1$ is a nitro group or a protective amino group, and $R^6$ and $R^7$ are the same as "substituents" of the "$C_{1-6}$ alkyl groups that may have one or more substituents" represented by $R^2$. $R^6$ and $R^7$ particularly represent substituted or unsubstituted heterocyclic groups, m is 0 to 3, and n is 1 or 2.

The production method shown in Reaction Scheme 3 is the same as that of the amine compound (1c) in Reaction Schemes 1 and 2. The method comprises the following four steps:

A first step in which an amino-containing compound shown in Formula (3b) is reacted with an elimination functional group $X^1$-containing compound shown in Formula (3a) to form a hydroxy-containing compound shown in Formula (3c);

a second step in which a compound shown in Formula (3d) is reacted with the hydroxy-containing compound (3c) to introduce an elimination functional group $X^2$, thereby forming a compound represented by Formula (3e);

a third step in which an amine compound (3f) is reacted with the elimination functional group $X^2$ to perform condensation, thereby forming a compound represented by Formula (3g); and a fourth step in which the compound (3g) obtained in the third step is subjected to nitro group reduction or deprotection of a protective group of amino group by an ordinary method, thereby forming an amine compound (3h).

First Step

Any elimination functional group can be used as $X^1$ of the compound (3a) in the first step. Examples thereof include halogen such as fluorine and chlorine, methanesulfonyloxy, p-toluenesulfonyloxy, and trifluoromethanesulfonyloxy.

In a suitable solvent, using 0.5 to 10 moles, and preferably 0.8 to 2 moles, of the amine compound shown in Formula (3b) or a salt thereof relative to 1 mole of the compound shown in (3a), reaction is conducted in the presence of 0.5 to 10 moles, and preferably 0.8 to 3 moles, of base relative to 1 mole of the compound shown in Formula (3a), at −20 to 180° C., and preferably at 0 to 150° C., thereby forming the hydroxy-containing compound shown in Formula (3c).

Any solvents can be used as long as they do not adversely affect the reaction. Examples of suitable solvents include a halogenated hydrocarbon such as dichloromethane and chloroform; an aromatic hydrocarbon such as toluene; an ether such as tetrahydrofuran; an ester such as ethyl acetate; an alcohol such as methanol and ethanol; water; acetonitrile; N,N-dimethylformamide; N,N-dimethylacetamide; N-methylpyrrolidone; dimethylsulfoxide; and pyridine. The solvents can be used singly or in a combination.

Examples of a base include inorganic bases such as sodium hydroxide, calcium hydroxide, sodium carbonate, potassium carbonate, and sodium hydride, and organic bases such as pyridine, 4-(N,N-dimethylamino)pyridine, triethylamine, diisopropylethylamine, 1,8-diazabicyclo[5.4.0]undec-7-en, and potassium tert-butoxide.

Second Step

In a suitable solvent, using 0.5 to 10 moles, and preferably 0.8 to 2 moles, of the elimination functional group-containing compound shown in Formula (3d) relative to 1 mole of the hydroxy-containing compound shown in (3c), the reaction is conducted in the presence of 0.5 to 10 moles, and preferably 0.8 to 3 moles, of base relative to 1 mole of the compound shown in Formula (3c), at −20 to 180° C., and preferably at 0 to 150° C., thereby forming the compound shown in Formula (3e).

Any solvents can be used as long as they do not adversely affect the reaction. Examples of suitable solvents include a halogenated hydrocarbon such as dichloromethane and chloroform; an aromatic hydrocarbon such as toluene; an ether such as tetrahydrofuran; an ester such as ethyl acetate; acetonitrile; N,N-dimethylformamide; N,N-dimethylacetamide; N-methylpyrrolidone; dimethylsulfoxide; and pyridine. The solvents can be used singly or in a combination.

Examples of a base include inorganic bases such as sodium hydroxide, calcium hydroxide, sodium carbonate, potassium carbonate, and sodium hydride, and organic bases such as pyridine, 4-(N,N-dimethylamino)pyridine, triethylamine, diisopropylethylamine, 1,8-diazabicyclo[5.4.0]undec-7-en, and potassium tert-butoxide.

Third Step

In a suitable solvent, using 0.5 to 10 moles, and preferably 0.8 to 3 moles, of the amine compound shown in Formula (3f) relative to 1 mole of the compound shown in (3e), the reaction is conducted in the presence of 0.5 to 10 moles, and preferably 0.8 to 3 moles, of base relative to 1 mole of the compound shown in Formula (3e), at −20 to 180° C., and preferably at 0 to 150° C., thereby forming the compound shown in Formula (3g).

Any solvents can be used as long as they do not adversely affect the reaction. Examples of suitable solvents include a halogenated hydrocarbon such as dichloromethane and chloroform; an aromatic hydrocarbon such as toluene; an ether such as tetrahydrofuran; an ester such as ethyl acetate; acetonitrile; N,N-dimethylformamide; N,N-dimethylacetamide; N-methylpyrrolidone; dimethylsulfoxide; and pyridine. The solvents can be used singly or in a combination.

Examples of a base include inorganic bases such as sodium hydroxide, calcium hydroxide, sodium carbonate, potassium carbonate, and sodium hydride, and organic bases such as pyridine, 4-(N,N-dimethylamino)pyridine, triethylamine, diisopropylethylamine, 1,8-diazabicyclo[5.4.0]undec-7-en, and potassium tert-butoxide.

Fourth Step

When $Z^1$ is a nitro group, reduction conditions are not limited as long as the nitro group is converted to an amino group by reduction. It is preferable that reaction conditions be selected considering properties of other functional groups of the nitro compound (3g).

Typical reduction methods include the following:

(A) In water, an alcohol such as methanol or ethanol, an ether such as tetrahydrofuran, or a mixture of solvents thereof, 0.01 to 10 moles, and preferably 0.03 to 5 moles, of a reduction catalyst such as reduced iron, tin chloride, or iron chloride is reacted in the presence of 0.3 to 30 moles, and preferably 0.5 to 20 moles, of an ammonium salt, such as ammonium chloride, hydrazine hydrate, hydrochloric acid, etc., relative to 1 mole of the nitro compound shown in Formula (3g), at 0 to 150° C., and preferably 20 to 120° C.

(B) In alcohols, ethers, esters such as ethyl acetate, organic acids such as formic acid and acetic acid, or a mixture of solvents thereof, hydrogen gas is reacted under ordinary pressure or high pressure in the presence of 0.001 to 1 mole, and preferably 0.01 to 0.3 mole, of a reduction catalyst, such as carbon-supported palladium, platinum oxide, and Raney nickel, relative to 1 mole of the nitro compound shown in Formula (3g), at 0 to 120° C., and preferably 20 to 100° C.; or 0.5 to 20 moles, and preferably 1 to 10 moles, of formic acid, ammonium formate, or cyclohexene relative to 1 mole of the nitro compound shown in Formula (3g) is used as a hydrogen source in place of hydrogen gas.

If $Z^1$ is a protective amino group, deprotection can be performed in the same manner as in the second step of Reaction Scheme 1 to obtain the amine compound (3h).

The compounds (3a), (3b), (3d), and (3f) used in Reaction Scheme 3 are known, or can be manufactured in accordance with a known method.

The amine compound (1c) in Reaction Scheme 1 or 2, i.e., the amine compound represented by Formula (4f), can be produced according to the method shown in Reaction Scheme 4 below.

Reaction Scheme 4

[Structures (4a), (4b), (4c), (4e), (4f) shown with reaction arrows labeled First Step, Second Step, and Third Step]

In Reaction Scheme 4, $X^1$, $Z^1$, $R^3$, and $R^4$ are the same as above, $R^8$ is the same as $R^5$ or a silyl protective group such as tert-butyldimethylsilyl, l is 0 to 3, and n is 1 or 2.

The production method shown in Reaction Scheme 4 includes the first step, in which an elimination functional group $X^1$-containing compound (4a) is reacted with an amino-containing ester compound shown in Formula (4b) to form an ester-containing compound shown in Formula (4c); the second step, in which an ester group of an ester-containing compound (4c) is deprotected, and then condensed with an amine compound shown in Formula (4d) by an ordinary method to form an amide compound shown in Formula (4e); and the third step, in which the compound (4e) is subjected to nitro group reduction or deprotection of a protective group of amino group by an ordinary method, thereby forming an amine compound (4f).

First Step

In this step, the ester-containing compound represented by Formula (4c) can be obtained in the same manner as in the first step of Reaction Scheme 3.

Second Step

In this step, the ester of the ester-containing compound shown in Formula (4c) is deprotected by an ordinary, known method, and then condensed with the amine compound shown in Formula (4d) or a salt thereof in the same manner as in the first step of Reaction Scheme 1 to form the amide compound represented by Formula (4e).

Third Step

In this step, $Z^1$ can be converted to an amino group in the same manner as in the fourth step of Reaction Scheme 3.

The compounds (4a), (4b), and (4d) used in Reaction Scheme 4 are known, or can be manufactured by a known method.

Of the compounds of the present invention, compounds having particular functional groups may be converted to other compounds of the invention by chemically modifying these groups, as shown in the following Reaction Scheme 5.

Reaction Scheme 5

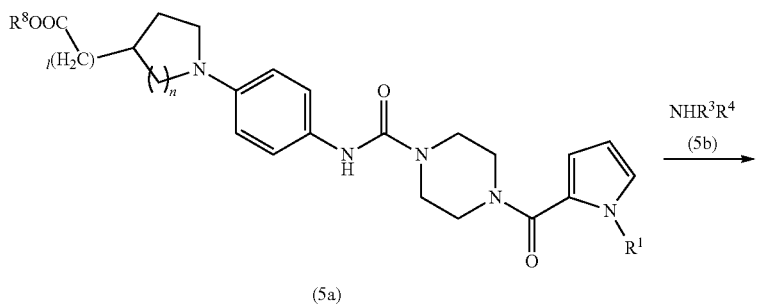

(5a)

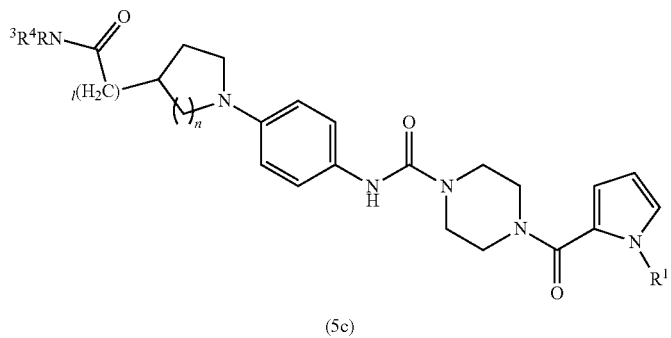

(5c)

In Reaction Scheme 5, $R^1$, $R^3$, $R^4$, $R^8$, n, and l are the same as above.

In the production method shown in Reaction Scheme 5, the carboxylic acid compound obtained by deprotecting the ester compound shown in Formula (5a), or an active species thereof is condensed in the same manner as in the first step of Reaction Scheme 1 with the amine compound represented by Formula (5b), to form the amide compound (5c).

If one or more asymmetric carbons are present in the compound (I), which is useful as an active ingredient of the medicine of the present invention, optical isomers due to asymmetric carbon atoms (enantiomers and diastereomers) and other isomers may be present. The present invention encompasses isomers that have been isolated and mixtures thereof.

The compound (I), which is useful as an active ingredient of the medicine of the present invention, encompasses pharmaceutically acceptable prodrugs. Pharmaceutically acceptable prodrugs are compounds having functional groups that can be converted, under chemical conditions, such as solvolysis, or under physiological conditions, into amino, hydroxy, carboxy, carbonyl, or like functional groups of the compound (I), which is an active ingredient of the medicine of the present invention. Representative functional groups of prodrugs include the groups mentioned in "Iyakuhin no Kaihatsu (Development of Pharmaceuticals)", Vol. 7, pp. 163-198, Hirokawa Publishing (1990).

The compound (I), which is useful as an active ingredient of the medicine of the present invention may form an acid addition salt or a salt with a base. Such salts are included in the present invention insofar as they are pharmaceutically acceptable. Specific examples thereof include acid addition salts with inorganic acids, such as hydrochloric acid, hydrobromic acid, hydroiodic acid, sulfuric acid, nitric acid, phosphoric acid, etc., or organic acids, such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, para-toluenesulfonic acid, glutamic acid, etc.; salts with inorganic bases, such as sodium, potassium, magnesium, calcium, aluminium, etc., organic bases such as methylamine, ethylamine, meglumine, ethanolamine, etc., or basic amino acids such as lysine, arginine, ornithine, etc.; and ammonium salts.

The present invention further encompasses the hydrates, solvates, and crystal polymorphs, of the compound (I), which is useful as an active ingredient of the medicine of the present invention, and pharmaceutically acceptable salts thereof.

When a pharmaceutical composition contains the piperazine compound or a salt thereof according to the present invention, a pharmaceutical carrier can be added, if required, thereby forming a suitable dosage form according to prevention and treatment purposes. Examples of the dosage form include oral preparations, injections, suppositories, ointments, patches, etc. Of these, oral preparations are preferable. Such dosage forms can be formed by a method conventionally known to persons skilled in the art.

As the pharmaceutical carrier, various conventional organic or inorganic carrier materials used as preparation materials may be blended as an excipient, binder, disintegrant, lubricant, or colorant in solid preparations, or as a solvent, solubilizing agent, suspending agent, isotonizing agent, buffer, or soothing agent in liquid preparations. Moreover, a pharmaceutical preparation additive, such as an antiseptic, anti-oxidant, colorant, sweetener, and stabilizer may also be used if required.

Oral solid preparations are prepared as follows. An excipient, optionally together with a binder, disintegrant, lubricant, colorant, sweetening/flavoring agent, etc., is added into the compound of the present invention to produce tablets, coated tablets, granules, powders, capsules, or the like, using an ordinary method.

Examples of excipients include lactose, sucrose, D-mannitol, glucose, starch, calcium carbonate, kaolin, microcrystalline cellulose, and silicic acid.

Examples of binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, and polyvinylpyrrolidone.

Examples of disintegrants include dry starch, sodium alginate, agar powder, sodium hydrogen carbonate, calcium carbonate, sodium lauryl sulfate, stearic acid monoglyceride, and lactose.

Examples of lubricants include purified talc, sodium stearate, magnesium stearate, borax, and polyethylene glycol.

Examples of colorants include titanium oxide and iron oxide.

Examples of sweetening/flavoring agents include sucrose, wild orange peel, citric acid, and tartaric acid.

Oral liquid preparations are produced as follows. A sweetening agent, buffer, stabilizer, sweetening flavoring agent, etc., is added into the compound of the present invention to produce an internal liquid medicine, a syrup, an elixir, or the like using an ordinary method. In this case, sweetening/flavoring agents as described above are usable. Examples of buffers include sodium citrate, and examples of stabilizers include tragacanth, gum arabic, and gelatin. If necessary, an eneteric coating or a coating to increase the persistence of effects can be provided by methods known for oral preparations. Examples of coating agents include hydroxypropylmethyl cellulose, ethyl cellulose, hydroxymethyl cellulose, hydroxypropyl cellulose, polyoxy ethylene glycol, and Tween 80 (a registered trademark).

Injections are prepared as follows. A pH adjuster, buffer, stabilizer, isotonizing agent, topical anesthetic, etc., is added into the compound of the present invention to produce a subcutaneous injection, an intramuscular injection, or an intravenous injection using an ordinary method. Examples of usable pH adjusters and buffers in this case include sodium citrate, sodium acetate, and sodium phosphate. Examples of usable stabilizers include sodium pyrosulfite, EDTA, thioglycolic acid, and thiolactic acid. Examples of usable topical anesthetics include procaine hydrochloride and lidocaine hydrochloride. Examples of usable isotonizing agents include sodium chloride, glucose, D-mannitol, and glycerin.

Suppositories are prepared as follows. A pharmaceutical carrier known in the art, such as polyethylene glycol, lanolin, cacao butter, and fatty acid triglyceride, is added into the compound of the present invention, optionally together with Tween 80 (a registered trademark) or a like surfactant, followed by production using an ordinary method.

Ointments are prepared as follows. An ordinary base, stabilizer, wetting agent, preservative, etc., is added as required into the compound of the present invention, and mixed and formulated using an ordinary method. Examples of bases include liquid paraffin, white petrolatum, white beeswax, octyldodecyl alcohol, and paraffin. Examples of preservatives include methyl parahydroxybenzoate, ethyl parahydroxybenzoate, and propyl parahydroxybenzoate.

Patches can be prepared by coating a general support with the above ointment, cream, gel, paste, etc., using an ordinary method. Examples of supports include woven or nonwoven fabrics made from cotton, staple fibers, and chemical fibers; and films and foam sheets of soft vinyl chloride, polyethylene, and polyurethane.

The amount of the compound of the present invention to be contained in such a dosage unit form varies depending on the condition of the patient or on the dosage form. The desirable amount in one dosage unit form is about 0.05 to about 1,000 mg in the case of an oral preparation, about 0.01 to about 500 mg in the case of an injection, and about 1 to about 1,000 mg in the case of a suppository.

The daily dose of the medicine in such a dosage form depends on the condition, body weight, age, gender, etc., of the patient. For example, the daily dose for an adult (body weight: 50 kg) may be generally about 0.05 to about 5,000 mg, and preferably 0.1 to 1,000 mg, and is preferably administered in one or in two to three divided doses per day.

Since the H-PGDS inhibiting action is attained in mammals, and especially man, by administrating a medicine containing the compound of the present invention, the compound of the present invention is useful in treating, preventing, or improving diseases caused by PGD2 generated by a synthase or metabolite thereof. The compound of the present invention can be administered to mammals including humans, monkeys, mice, rats, rabbits, dogs, cats, cows, horses, pigs, and sheep. The compound can be administered to mammals orally or non-orally by an ordinary method.

Examples of diseases to be treated, prevented, or improved by a pharmaceutical agent containing the compound of the present invention include allergic disease, inflammatory disease, and myodegenerative disease.

Examples of allergic diseases include bronchial asthma, pollinosis, allergic rhinitis, sinusitis, otitis media, allergic conjunctivitis, spring catarrh, atopic dermatitis, contact dermatitis, and food allergies. Of these, bronchial asthma, pollinosis, allergic rhinitis, and sinusitis are preferable. Examples of inflammatory diseases include chronic obstructive pulmonary disease, interstitial pneumonia, hypersensitivity pneumonitis, eosinophilic pneumonia, articular rheumatism, degenerative arthritis, multiple sclerosis, inflammatory bowel disease, skin diseases (psoriasis, eczema, erythema, itch syndrome, pimples, etc.), post-PTCA restenosis, chronic obstructive arterial disease, reperfusion injury, and graft rejection reaction.

Examples of myodegenerative diseases include muscular dystrophy such as Duchenne muscular dystrophy, which is a myogenic disease, Becker's muscular dystrophy, limb-girdle muscular dystrophy, and congenital muscular dystrophy; various myopathies such as congenital myopathy; amyotrophic lateralsclerosis, which is a neurogenic muscular atrophy; muscle strain; cardiomyopathy (cardiac infarction); and diabetic peripheral vascular disorders (vascular smooth muscle disorders). Preferable examples of myodegenerative diseases to be treated, prevented, or improved by a medicine containing the compound of the present invention include Duchenne muscular dystrophy, Becker's muscular dystrophy, and amyotrophic lateralsclerosis.

Furthermore, the medicine containing the compound of the present invention is expected to improve the treatment and prevention of mucus secretion problems, reproductive problems, blood coagulation disorders, sleep disorders, pain, vision problems, obesity, immunopathy, and autoimmune diseases; to prevent exacerbation of Alzheimer disease or brain damage, and/or improve the prognosis after brain damage. In addition, since it can inhibit cell neoplastic transformation and metastatic tumor growth, it is also useful in cancer therapy.

Moreover, it is useful in the treatment and/or prevention of proliferative disorders due to PGD2 or its metabolites, such as fibroblast proliferation, diabetic retinopathy, and tumor angiogenesis. Furthermore, since it can suppress PGD2-induced smooth muscle contraction, it can also be used in the treatment and/or prevention of infertility, dysmenorrhea, premature delivery, and eosinophile-leucocyte-related disorders.

EXAMPLES

The present invention is described in detail below with reference to Reference Examples, Examples, and Test Examples, which are not intended to limit the scope of the invention.

In the following description, 1H-NMR spectra were measured using TMS (tetramethylsilane) as an internal standard, and the chemical shifts are indicated by δ (ppm). With respect to the chemical shifts, absorption patterns, coupling constants (J), and numbers of protons are indicated in parentheses.

The following symbols are used for absorption patterns: s=singlet, d=doublet, t=triplet, q=quartet, dd=double doublet, m=multiplet, br=broad, and brs=broad singlet.

Moreover, the following symbols are used for structural formulas of compounds: Me=methyl and Et=ethyl.

Example 1

N-(4-(4-hydroxypiperidin-1-yl)-phenyl)-4-((1-methylpyrrol-2-yl)-carbonyl)-1-piperazinecarboxamide Example 1(1)

4-hydroxy-N-(4-nitrophenyl)piperidine 4-chloronitrobenzene (31.5 g, 200 mmol) was dissolved in N,N-dimethylacetamide (80 ml), and potassium carbonate (35.9 g, 260 mmol) and 4-hydroxypiperidine (22.3 g, 220 mmol) were added thereto, followed by stirring under heat at 130° C. for 3 hours. After cooling to room temperature, water was added to the mixture, and the precipitate was collected by filtration. The obtained solid was dried under reduced pressure, thereby obtaining 4-hydroxy-N-(4-nitrophenyl)piperidine (41.3 g, 93%) as a yellow solid.

1H-NMR (CDCl3): δ (ppm) 1.52-1.74 (m, 2H), 1.92-2.04 (m, 2H), 3.14-3.35 (m, 2H), 3.73-4.08 (m, 3H), 6.82 (d, J=9.6 Hz, 2H), 8.11 (d, J=9.6 Hz, 2H)

Example 1(2)

4-hydroxy-N-(4-aminophenyl)piperidine

The 4-hydroxy-N-(4-nitrophenyl)piperidine (11.1 g, 50 mmol) obtained in Example 1(1) was dissolved in methanol (100 ml) and tetrahydrofuran (50 ml), and 10% palladium-carbon (8.0 g) was added thereto, followed by stirring at room temperature in an atmosphere of hydrogen gas for 7 hours. After the insoluble material was filtered with Celite, the filtrate was concentrated under reduced pressure, diethyl ether was added to the obtained residue, and the precipitate was collected by filtration, thereby obtaining 4-hydroxy-N-(4-aminophenyl)piperidine (9.25 g, 94%) as a reddish-purple solid.

1H-NMR (CDCl3): δ (ppm) 1.65-1.77 (m, 2H), 1.94-2.11 (m, 2H), 2.71-2.85 (m, 2H), 3.23-3.92 (m, 5H), 6.64 (d, J=8.9 Hz, 2H), 6.83 (d, J=8.9 Hz, 2H)

Example 1(3)

N-(4-(4-hydroxypiperidin-1-yl)-phenyl)-4-((1-methylpyrrol-2-yl)-carbonyl)-1-piperazinecarboxamide 4-nitrophenyl chloroformate (242 mg, 1.2 mmol) was dissolved in tetrahydrofuran (3 ml), and a tetrahydrofuran (4 ml) solution of the 4-hydroxy-N-(4-aminophenyl)piperidine (211 mg, 1.0 mmol) obtained in Example 1(2) was added dropwise at −30° C. After stirring for 30 minutes at the same temperature, 1-[(1-methyl-1H-pyrrol-2-yl)carbonyl]piperazine hydrochloride (252 mg, 1.1 mmol) and triethylamine (0.49 ml, 3.5 mmol) were added to the mixture, followed by stirring at room temperature for 17 hours. A saturated sodium bicarbonate aqueous solution was added to the reaction mixture, followed by extraction with ethyl acetate. The organic layer was washed with water and saturated sodium chloride, and dried over anhydrous sodium sulfate. After the desiccant was filtered off, the residue obtained by evaporation under reduced pressure was purified using medium pressure silica gel flash column chromatography (NH silica gel, methanol:chloroform=0:1 to 1:50), thereby obtaining N-(4-(4-hydroxypiperidin-1-yl)-phenyl)-4-((1-methylpyrrol-2-yl)-carbonyl)-1-piperazinecarboxamide (256 mg, 62%) as a milky-white solid.

1H-NMR (CDCl3): δ (ppm) 1.60-1.78 (m, 2H), 1.93-2.08 (m, 2H), 2.80-2.95 (m, 2H), 3.40-3.63 (m, 6H), 3.75-3.90 (m, 5H), 3.80 (s, 3H), 6.08-6.15 (m, 1H), 6.25 (brs, 1H), 6.32-6.40 (m, 1H), 6.70-6.77 (m, 1H), 6.90 (d, J=8.9 Hz, 2H), 7.21 (d, J=8.9 Hz, 2H)

Example 2

4-((((1-methylpyrrol-2-yl)-carbonyl)-1-piperazinyl)carbonyl)amino-4-phenylpiperidine-4-carboxylic acid

Example 2(1)

1-(4-nitrophenyl)piperidine-4-carboxylic acid ethyl ester

Following the procedure of Example 1(1), isonipecotic acid ethyl ester was used instead of 4-hydroxypiperidine, thereby obtaining 1-(4-nitrophenyl)piperidine-4-carboxylic acid ethyl ester (95%) as a yellow solid.

1H-NMR (CDCl3): δ (ppm) 1.27 (t, J=7.2 Hz, 3H), 1.80-1.90 (m, 2H), 2.00-2.08 (m, 2H), 2.54-2.62 (m, 1H), 3.01-3.14 (m, 2H), 3.84-3.92 (m, 2H), 4.17 (q, J=7.2 Hz, 2H), 6.83 (d, J=7.2 Hz, 2H), 8.11 (d, J=7.2 Hz, 2H)

Example 2(2)

1-(4-aminophenyl)piperidine-4-carboxylic acid ethyl ester

Following the procedure of Example 1(2), the 1-(4-nitrophenyl)piperidine-4-carboxylic acid ethyl ester obtained in Example 2(1) was used instead of 4-hydroxy-N-(4-nitrophenyl)piperidine, thereby obtaining 1-(4-aminophenyl)piperidine-4-carboxylic acid ethyl ester (quant.) as a reddish-brown oil.

1H-NMR (CDCl3): δ (ppm) 1.27 (t, J=7.1 Hz, 3H), 1.78-2.13 (m, 4H), 2.30-2.47 (m, 1H), 2.55-2.75 (m, 2H), 3.20-3.64 (m, 4H), 4.15 (q, J=7.1 Hz, 2H), 6.64 (d, J=8.9 Hz, 2H), 6.82 (d, J=8.9 Hz, 2H)

Example 2(3)

4-((((1-methylpyrrol-2-yl)-carbonyl)-1-piperazinyl)carbonyl)amino-4-phenylpiperidine-4-carboxylic acid ethyl ester Following the procedure of Example 1(3), the 1-(4-aminophenyl)piperidine-4-carboxylic acid ethyl ester obtained in Example 2(2) was used instead of 4-hydroxy-N-(4-aminophenyl)piperidine, thereby obtaining 4-((((1-methylpyrrol-2-yl)-carbonyl)-1-piperazinyl)-carbonyl)amino-4-phenylpiperidine-4-carboxylic acid ethyl ester (80%) as a milky-white solid.

1H-NMR (CDCl3): δ (ppm) 1.27 (t, J=7.1 Hz, 3H), 1.75-2.12 (m, 4H), 2.33-2.48 (m, 1H), 2.67-2.84 (m, 2H), 3.42-3.65 (m, 6H), 3.70-3.93 (m, 4H), 3.79 (s, 3H), 4.15 (q, J=7.1 Hz, 2H), 6.06-6.15 (m, 1H), 6.30-6.40 (m, 1H), 6.41 (brs, 1H), 6.69-6.76 (m, 1H), 6.88 (d, J=9.0 Hz, 2H), 7.22 (d, J=9.0 Hz, 2H)

Example 2(4)

4-((((1-methylpyrrol-2-yl)-carbonyl)-1-piperazinyl)carbonyl)amino-4-phenylpiperidine-4-carboxylic acid The 4-((((1-methylpyrrol-2-yl)-carbonyl)-1-piperazinyl)carbonyl)amino-4-phenylpiperidine-4-carboxylic acid ethyl ester (234 mg, 0.5 mmol) obtained in Example 2(3) was dissolved in tetrahydrofuran (1.5 ml) and ethanol (1.5 ml), and a 2 N sodium hydroxide aqueous solution (1.4 ml, 2.8 mmol) was added thereto, followed by stirring at room temperature for 5 hours. After the reaction mixture was cooled to 0° C., a 2 N hydrochloric acid (1.4 ml, 2.8 mmol) was added to the reaction mixture, followed by extraction with a mixed solvent of methanol:chloroform (1:10). The organic layer was washed with water and saturated sodium chloride, and dried over anhydrous sodium sulfate. After the desiccant was filtered off, the residue obtained by evaporation under reduced pressure was washed with diethyl ether, thereby obtaining 4-((((1-methylpyrrol-2-yl)-carbonyl)-1-piperazinyl)-carbonyl)amino-4-phenylpiperidine-4-carboxylic acid (167 mg, 75%) as a milky-white solid.

1H-NMR (CDCl3): δ (ppm) 1.79-2.13 (m, 4H), 2.38-2.54 (m, 1H), 2.65-2.87 (m, 2H), 3.45-3.67 (m, 6H), 3.71-3.94 (m, 4H), 3.80 (s, 3H), 6.05-6.14 (m, 1H), 6.28-6.46 (m, 2H), 6.68-6.77 (m, 1H), 6.90 (d, J=8.9 Hz, 2H), 7.21 (d, J=8.9 Hz, 2H)

Example 3

4-((1-methylpyrrol-2-yl)-carbonyl)-N-(4-(4-morpholin-1-yl-carbonylpiperidin-1-yl)-phenyl)-1-piperazinecarboxamide

Example 3(1)

1-(4-nitrophenyl)piperidine-4-carboxylic acid

The 1-(4-nitrophenyl)piperidine-4-carboxylic acid ethyl ester (2.78 g, 10 mmol) obtained in Example 2(1) was dissolved in ethanol (10 ml), and a 4 N sodium hydroxide aqueous solution (5 ml, 20 mmol) was added thereto. The mixture was refluxed under heat for 1 hour. After cooling to room temperature, water (30 ml) and 2 N hydrochloric acid (10 ml) were added to the mixture, and the precipitate was collected by filtration, thereby obtaining 1-(4-nitrophenyl)piperidine-4-carboxylic acid (2.47 g, 97%) as a yellow solid.

1H-NMR (DMSO-d6): δ (ppm) 1.49-1.68 (m, 2H), 1.84-2.00 (m, 2H), 2.50-2.66 (m, 1H), 3.01-3.19 (m, 2H), 3.90-4.05 (m, 2H), 7.02 (d, J=9.4 Hz, 2H), 8.03 (d, J=9.4 Hz, 2H), 12.28 (br, 1H)

Example 3(2)

1-(4-nitrophenyl)piperidine-4-morpholinecarboxamide

The 1-(4-nitrophenyl)piperidine-4-carboxylic acid (10.1 g, 40 mmol) obtained in Example 3(1) was dissolved in N,N-dimethylformamide (25 ml), and morpholine (5.2 g, 60 mmol), 1-ethyl-3-(3-dimethylaminopropyl)carbodiimide hydrochloride (9.2 g, 48 mmol), and 1-hydroxybenzotriazole monohydrate (6.7 g, 44 mmol) were added thereto, followed by stirring overnight under heat at 70° C. After cooling to room temperature, water was added thereto, and the precipitate was collected by filtration and dried under heat under reduced pressure, thereby obtaining 1-(4-nitrophenyl)piperidine-4-morpholinecarboxamide (12.1 g, 95%) as a yellow solid.

1H-NMR (CDCl3): δ (ppm) 1.80-2.08 (m, 4H), 2.68-2.81 (m, 1H), 2.95-3.13 (m, 2H), 3.46-3.78 (m, 8H), 3.89-4.07 (m, 2H), 6.81 (d, J=8.4 Hz, 2H), 8.11 (d, J=8.4 Hz, 2H)

Example 3(3)

1-(4-aminophenyl)piperidine-4-morpholinecarboxamide

Following the procedure of Example 1(2), the 1-(4-nitrophenyl)piperidine-4-morpholinecarboxamide obtained in Example 3(2) was used instead of 4-hydroxy-N-(4-nitrophenyl)piperidine, thereby obtaining 1-(4-aminophenyl)piperidine-4-morpholinecarboxamide (90%) as a reddish-purple solid.

1H-NMR (CDCl3): δ (ppm) 1.72-1.89 (m, 2H), 1.92-2.15 (m, 2H), 2.45-2.74 (m, 3H), 3.28-3.80 (m, 12H), 6.65 (d, J=8.9 Hz, 2H), 6.82 (d, J=8.9 Hz, 2H)

Example 3(4)

4-((1-methylpyrrol-2-yl)-carbonyl)-N-(4-(4-morpholin-1-yl-carbonylpiperidin-1-yl)-phenyl)-1-piperazinecarboxamide Following the procedure of Example 1(3), the 1-(4-aminophenyl)piperidine-4-morpholinecarboxamide obtained in Example 3(3) was used instead of 4-hydroxy-N-(4-aminophenyl)piperidine, thereby obtaining 4-((1-methylpyrrol-2-yl)-carbonyl)-N-(4-(4-morpholin-1-yl-carbonylpiperidin-1-yl)-phenyl)-1-piperazinecarboxamide (82%) as a milky-white solid.

1H-NMR (CDCl3): δ (ppm) 1.72-2.12 (m, 4H), 2.47-2.78 (m, 3H), 3.43-3.90 (m, 18H), 3.80 (s, 3H), 6.07-6.16 (m, 1H), 6.33-6.39 (m, 1H), 6.44 (brs, 1H), 6.69-6.78 (m, 1H), 6.88 (d, J=8.9 Hz, 2H), 7.22 (d, J=8.9 Hz, 2H)

Example 4

4-((1-methylpyrrol-2-yl)-carbonyl)-N-(4-(4-morpholinomethylpiperidin-1-yl)-phenyl)-1-piperazinecarboxamide Example 4(1)

4-hydroxymethyl-N-(4-nitrophenyl)piperidine

Following the procedure of Example 1(1), 4-hydroxymethylpiperidine was used instead of 4-hydroxypiperidine, thereby obtaining 4-hydroxymethyl-N-(4-nitrophenyl)piperidine (97%) as a yellow solid.

1H-NMR (CDCl3): δ (ppm) 1.23-1.48 (m, 3H), 1.70-1.97 (m, 3H), 2.90-3.07 (m, 2H), 3.56 (t, J=5.7 Hz, 2H), 3.93-4.07 (m, 2H), 6.81 (d, J=9.4 Hz, 2H), 8.11 (d, J=9.4 Hz, 2H)

Example 4(2)

4-tosyloxymethyl-N-(4-nitrophenyl)piperidine

The 4-hydroxymethyl-N-(4-nitrophenyl)piperidine (47.3 g, 200 mmol) obtained in Example 4(1) was dissolved in pyridine (300 ml), and p-toluenesulfonyl chloride (45.8 g, 240 mmol) was added thereto under ice-cooling, followed by stirring for 4 hours. Water was added to the reaction mixture, and the precipitate was collected by filtration. The obtained solid was dried under reduced pressure, thereby obtaining 4-tosyloxymethyl-N-(4-nitrophenyl)piperidine (72.7 g, 93%) as a yellow solid.

1H-NMR (CDCl3): δ (ppm) 1.20-1.40 (m, 2H), 1.75-1.90 (m, 2H), 1.90-2.12 (m, 1H), 2.46 (s, 3H), 2.87-3.03 (m, 2H), 3.90 (d, J=6.4 Hz, 2H), 3.90-4.02 (m, 2H), 6.78 (d, J=9.4 Hz, 2H), 7.36 (d, J=8.4 Hz, 2H), 7.79 (d, J=8.4 Hz, 2H), 8.09 (d, J=9.4 Hz, 2H)

Example 4(3)

4-morpholinomethyl-N-(4-nitrophenyl)piperidine

The 4-tosyloxymethyl-N-(4-nitrophenyl)piperidine (39.0 g, 100 mmol) obtained in Example 4(2) was dissolved in methyl ethyl ketone (150 ml), and sodium iodide (45.0 g, 300 mmol) was added thereto, followed by stirring at room temperature for 4 days. Ethyl acetate was added to the reaction mixture, and the insoluble material was filtered with Celite. Subsequently, the organic layer was washed with water and saturated sodium chloride, and dried over anhydrous sodium sulfate. After the desiccant was filtered off, diisopropyl ether was added to the residue obtained by evaporation under reduced pressure, and the precipitate was collected by filtration, thereby obtaining crude iodide. The obtained crude iodide was dissolved in acetonitrile (150 ml), and potassium carbonate (19.7 g, 143 mmol) and morpholine (12.4 ml, 143 mmol) were added thereto, followed by stirring at room temperature for 2 days. Water was added to the reaction mixture, followed by extraction with ethyl acetate. Subsequently, the organic layer was washed with water and saturated sodium chloride, and dried over anhydrous sodium sulfate. After the desiccant was filtered off, the residue obtained by evaporation under reduced pressure was purified using medium pressure silica gel flash column chromatography (methanol:chloroform=0:1 to 1:30), thereby obtaining 4-morpholinomethyl-N-(4-nitrophenyl)piperidine (16.2 g, 53% in 2 steps) as a yellow solid.

1H-NMR (CDCl3): δ (ppm) 1.17-1.38 (m, 2H), 1.70-2.00 (m, 3H), 2.21 (d, J=7.1 Hz, 2H), 2.32-2.53 (m, 4H), 2.86-3.05 (m, 2H), 3.62-3.78 (m, 4H), 3.86-4.05 (m, 2H), 6.80 (d, J=9.6 Hz, 2H), 8.10 (d, J=9.6 Hz, 2H)

Example 4(4)

4-morpholinomethyl-N-(4-aminophenyl)piperidine

Following the procedure of Example 1(2), the 4-morpholinomethyl-N-(4-nitrophenyl)piperidine obtained in Example 4(3) was used instead of 4-hydroxy-N-(4-nitrophenyl)piperidine, thereby obtaining 4-morpholinomethyl-N-(4-aminophenyl)piperidine (97%) as a reddish-purple solid.
1H-NMR (CDCl3): δ (ppm) 1.25-1.73 (m, 3H), 1.80-1.95 (m, 2H), 2.16-2.70 (m, 8H), 3.27-3.85 (m, 8H), 6.64 (d, J=8.6 Hz, 2H), 6.84 (d, J=8.6 Hz, 2H)

Example 4(5)

4-((1-methylpyrrol-2-yl)-carbonyl)-N-(4-(4-morpholinomethylpiperidin-1-yl)-phenyl)-1-piperazinecarboxamide Following the procedure of Example 1(3), the 4-morpholinomethyl-N-(4-aminophenyl)piperidine obtained in Example 4(4) was used instead of 4-hydroxy-N-(4-aminophenyl)piperidine, thereby obtaining 4-((1-methylpyrrol-2-yl)-carbonyl)-N-(4-(4-morpholinomethylpiperidin-1-yl)-phenyl)-1-piperazinecarboxamide (72%) as a milky-white solid.
1H-NMR (CDCl3): δ (ppm) 1.22-1.46 (m, 2H), 1.53-1.75 (m, 1H), 1.81-1.98 (m, 2H), 2.22 (d, J=7.1 Hz, 2H), 2.33-2.51 (m, 4H), 2.57-2.74 (m, 2H), 3.45-3.93 (m, 14H), 3.80 (s, 3H), 6.08-6.14 (m, 1H), 6.32 (brs, 1H), 6.30-6.41 (m, 1H), 6.70-6.75 (m, 1H), 6.89 (d, J=9.1 Hz, 2H), 7.20 (d, J=9.1 Hz, 2H)

Example 5

4-((1-methylpyrrol-2-yl)-carbonyl)-N-(4-(3-(2-(1,2,4-triazol-1-yl)-ethyl)pyrrolidin-1-yl)-phenyl)-1-piperazinecarboxamide Example 5(1)

3-[2-(1,2,4-triazol-1-yl)-ethyl]-N-(4-nitrophenyl)pyrrolidine

The 4-tosyloxymethyl-N-(4-nitrophenyl)piperidine (39.0 g, 100 mmol) obtained in Example 4(2) was dissolved in methyl ethyl ketone (150 ml), and sodium iodide (45.0 g, 300 mmol) was added thereto, followed by stirring at room temperature for 5 days. Ethyl acetate was added to the reaction mixture, and the insoluble material was filtered with Celite. Subsequently, the organic layer was washed with water and saturated sodium chloride, and dried over anhydrous sodium sulfate. After the desiccant was filtered off, diisopropyl ether was added to the residue obtained by evaporation under reduced pressure, and the precipitate was collected by filtration, thereby obtaining crude iodide. The obtained crude iodide was dissolved in acetonitrile (160 ml) and water (40 ml), and potassium carbonate (24.9 g, 180 mmol) and 1,2,4-triazole (9.32 g, 134 mmol) were added thereto, followed by stirring at 80° C. for 6 hours. After the reaction mixture was allowed to cool to room temperature, water was added thereto, and the precipitate was collected by filtration and dried. The obtained solid was purified using medium pressure silica gel flash column chromatography (methanol:chloroform=0:1 to 1:30), thereby obtaining 3-[2-(1,2,4-triazol-1-yl)ethyl]-N-(4-nitrophenyl)pyrrolidine (16.4 g, 63% in 2 steps) as a yellow solid.
1H-NMR (CDCl3): δ (ppm) 1.55-1.80 (m, 1H), 2.00-2.35 (m, 4H), 2.97-3.14 (m, 1H), 3.31-3.64 (m, 3H), 4.30 (t, J=7.0 Hz, 2H), 6.44 (d, J=9.4 Hz, 2H), 7.97 (s, 1H), 8.11 (d, J=9.4 Hz, 2H), 8.12 (s, 1H)

Example 5(2)

3-[2-(1,2,4-triazol-1-yl)ethyl]-N-(4-aminophenyl)pyrrolidine

Following the procedure of Example 1(2), the 3-[2-(1,2,4-triazol-1-yl)-ethyl]-N-(4-nitrophenyl)pyrrolidine obtained in Example 5(1) was used instead of 4-hydroxy-N-(4-nitrophenyl)piperidine, thereby obtaining 3-[2-(1,2,4-triazol-1-yl)-ethyl]-N-(4-aminophenyl)pyrrolidine (96%) as a reddish-purple solid.
1H-NMR (CDCl3): δ (ppm) 1.65-1.87 (m, 1H), 2.00-2.43 (m, 4H), 2.75-3.70 (m, 6H), 4.25 (t, J=7.1 Hz, 2H), 6.44 (d, J=8.4 Hz, 2H), 6.68 (d, J=8.4 Hz, 2H), 8.00 (s, 1H), 8.08 (s, 1H)

Example 5(3)

4-((1-methylpyrrol-2-yl)-carbonyl)-N-(4-(3-(2-(1,2,4-triazol-1-yl)-ethyl)pyrrolidin-1-yl)-phenyl)-1-piperazinecarboxamide Following the procedure of Example 1(3), 3-[2-(1,2,4-triazol-1-yl)-ethyl]-N-(4-aminophenyl)pyrrolidine obtained in Example 5(2) was used instead of 4-hydroxy-N-(4-aminophenyl)piperidine, thereby obtaining 4-((1-methylpyrrol-2-yl)-carbonyl)-N-(4-(3-(2-(1,2,4-triazol-1-yl)-ethyl)pyrrolidin-1-yl)-phenyl)-1-piperazinecarboxamide (62%) as a milky-white solid.
1H-NMR (CDCl3): δ (ppm) 1.62-1.78 (m, 1H), 2.02-2.38 (m, 4H), 2.89-3.03 (m, 1H), 3.22-3.67 (m, 7H), 3.77-3.94 (m, 4H), 3.80 (s, 3H), 4.26 (t, J=7.1 Hz, 2H), 6.07-6.15 (m, 1H), 6.19 (brs, 1H), 6.33-6.41 (m, 1H), 6.48 (d, J=8.9 Hz, 2H), 6.70-6.78 (m, 1H), 7.16 (d, J=8.9 Hz, 2H), 7.96 (s, 1H), 8.09 (s, 1H)

Example 6

4-((1-methylpyrrol-2-yl)-carbonyl)-N-(4-(4-morpholinoethylpiperidin-1-yl)-phenyl)-1-piperazinecarboxamide Example 6(1)

4-hydroxyethyl-N-(4-nitrophenyl)piperidine

Following the procedure of Example 1(1), 4-hydroxyethylpiperidine was used instead of 4-hydroxypiperidine, thereby obtaining 4-hydroxyethyl-N-(4-nitrophenyl)piperidine (100%) as a yellow solid.
1H-NMR (CDCl3): δ (ppm) 1.18-1.40 (m, 3H), 1.47-1.92 (m, 5H), 2.85-3.03 (m, 2H), 3.63-3.78 (m, 2H), 3.85-4.02 (m, 2H), 6.77 (d, J=9.4 Hz, 2H), 8.07 (d, J=9.4 Hz, 2H)

Example 6(2)

4-tosyloxyethyl-N-(4-nitrophenyl)piperidine

Following the procedure of Example 4(2), the 4-hydroxyethyl-N-(4-nitrophenyl)piperidine obtained in Example 6(1)

was used instead of 4-hydroxymethyl-N-(4-nitrophenyl)piperidine, thereby obtaining 4-tosyloxyethyl-N-(4-nitrophenyl)piperidine (93%) as a yellow solid.

1H-NMR (CDCl3): δ (ppm) 1.13-1.35 (m, 2H), 1.55-1.84 (m, 5H), 2.46 (s, 3H), 2.82-3.01 (m, 2H), 3.84-4.00 (m, 2H), 4.10 (t, J=6.1 Hz, 2H), 6.78 (d, J=9.4 Hz, 2H), 7.36 (d, J=8.4 Hz, 2H), 7.80 (d, J=8.4 Hz, 2H), 8.10 (d, J=9.4 Hz, 2H)

Example 6(3)

4-morpholinoethyl-N-(4-nitrophenyl)piperidine

The 4-tosyloxyethyl-N-(4-nitrophenyl)piperidine (2.02 g, 5.0 mmol) obtained in Example 6(2) was dissolved in acetonitrile (20 ml), and potassium carbonate (1.38 g, 10 mmol) and morpholine (0.65 ml, 7.5 mmol) were added thereto, followed by stirring at 80° C. for 15 hours. After the reaction mixture was allowed to cool to room temperature, ethyl acetate was added to the reaction mixture, and the organic layer was washed with water and saturated sodium chloride, and dried over anhydrous sodium sulfate. After the desiccant was filtered off, the residue obtained by evaporation under reduced pressure was purified using medium pressure silica gel flash column chromatography (methanol:chloroform=1:50 to 1:20), thereby obtaining 4-morpholinoethyl-N-(4-nitrophenyl)piperidine (1.23 g, 77%) as a yellow solid.

1H-NMR (CDCl3): δ (ppm) 1.17-1.70 (m, 5H), 1.73-1.88 (m, 2H), 2.29-2.52 (m, 6H), 2.84-3.03 (m, 2H), 3.60-3.78 (m, 4H), 3.85-4.03 (m, 2H), 6.77 (d, J=9.4 Hz, 2H), 8.08 (d, J=9.4 Hz, 2H)

Example 6(4)

4-morpholinoethyl-N-(4-aminophenyl)piperidine

Following the procedure of Example 1(2), the 4-morpholinoethyl-N-(4-nitrophenyl)piperidine obtained in Example 6(3) was used instead of 4-hydroxy-N-(4-nitrophenyl)piperidine, thereby obtaining 4-morpholinoethyl-N-(4-aminophenyl)piperidine (83%) as a reddish-purple solid.

1H-NMR (CDCl3): δ (ppm) 1.28-1.98 (m, 7H), 2.32-2.73 (m, 8H), 3.20-3.90 (m, 8H), 6.62 (d, J=8.8 Hz, 2H), 6.80 (d, J=8.8 Hz, 2H)

Example 6(5)

4-((1-methylpyrrol-2-yl)-carbonyl)-N-(4-(4-morpholinoethylpiperidin-1-yl)-phenyl)-1-piperazinecarboxamide Following the procedure of Example 1(3), the 4-morpholinoethyl-N-(4-aminophenyl)piperidine obtained in Example 6(4) was used instead of 4-hydroxy-N-(4-aminophenyl)piperidine, thereby obtaining 4-((1-methylpyrrol-2-yl)-carbonyl)-N-(4-(4-morpholinoethylpiperidin-1-yl)-phenyl)-1-piperazinecarboxamide (88%) as a milky-white solid.

1H-NMR (CDCl3): δ (ppm) 1.30-1.55 (m, 5H), 1.70-1.89 (m, 2H), 2.34-2.75 (m, 8H), 3.47-3.90 (m, 14H), 3.80 (s, 3H), 6.05-6.13 (m, 1H), 6.27 (brs, 1H), 6.32-6.40 (m, 1H), 6.68-6.75 (m, 1H), 6.89 (d, J=8.9 Hz, 2H), 7.20 (d, J=8.9 Hz, 2H)

Example 7

4-((1-methylpyrrol-2-yl)-carbonyl)-N-(4-(4-(2-(1,2,3-triazol-1-yl)-ethyl)piperidin-1-yl)-phenyl)-1-piperazinecarboxamide Example 7(1)

4-[2-(1,2,3-triazol-1-yl)-ethyl]-N-(4-nitrophenyl)piperidine

Following the procedure of Example 6(3), 1,2,3-triazole was used instead of morpholine, thereby obtaining 4-[2-(1,2,3-triazol-1-yl)-ethyl]-N-(4-nitrophenyl)piperidine (39%) as a yellow solid.

1H-NMR (CDCl3): δ (ppm) 1.25-1.72 (m, 3H), 1.77-2.05 (m, 4H), 2.84-3.05 (m, 2H), 3.87-4.04 (m, 2H), 4.49 (t, J=7.1 Hz, 2H), 6.80 (d, J=9.5 Hz, 2H), 7.56 (d, J=0.8 Hz, 1H), 7.73 (d, J=0.8 Hz, 1H), 8.10 (d, J=9.5 Hz, 2H)

Example 7(2)

4-[2-(1,2,3-triazol-1-yl)-ethyl]-N-(4-aminophenyl)piperidine

Following the procedure of Example 1(2), the 4-[2-(1,2,3-triazol-1-yl)-ethyl]-N-(4-nitrophenyl)piperidine obtained in Example 7(1) was used instead of 4-hydroxy-N-(4-nitrophenyl)piperidine, thereby obtaining 4-[2-(1,2,3-triazol-1-yl)-ethyl]-N-(4-aminophenyl)piperidine (91%) as a reddish-purple solid.

1H-NMR (CDCl3): δ (ppm) 1.23-1.60 (m, 3H), 1.65-2.10 (m, 4H), 2.44-2.73 (m, 2H), 3.10-3.75 (m, 4H), 4.46 (t, J=7.4 Hz, 2H), 6.63 (d, J=8.7 Hz, 2H), 6.81 (d, J=8.7 Hz, 2H), 7.55 (s, 1H), 7.71 (s, 1H)

Example 7(3)

4-((1-methylpyrrol-2-yl)-carbonyl)-N-(4-(4-(2-(1,2,3-triazol-1-yl)-ethyl)piperidin-1-yl)-phenyl)-1-piperazinecarboxamide Following the procedure of Example 1(3), the 4-[2-(1,2,3-triazol-1-yl)-ethyl]-N-(4-aminophenyl)piperidine obtained in Example 7(2) was used instead of 4-hydroxy-N-(4-aminophenyl)piperidine, thereby obtaining 4-((1-methylpyrrol-2-yl)-carbonyl)-N-(4-(4-(2-(1,2,3-triazol-1-yl)-ethyl)piperidin-1-yl)-phenyl)-1-piperazinecarboxamide (50%) as a milky-white solid.

1H-NMR (CDCl3): δ (ppm) 1.31-1.53 (m, 3H), 1.72-2.00 (m, 4H), 2.55-2.78 (m, 2H), 3.46-3.66 (m, 6H), 3.73-3.92 (m, 4H), 3.80 (s, 3H), 4.47 (t, J=7.4 Hz, 2H), 6.05-6.14 (m, 1H), 6.32 (brs, 1H), 6.28-6.43 (m, 1H), 6.69-6.76 (m, 1H), 6.88 (d, J=9.0 Hz, 2H), 7.21 (d, J=9.0 Hz, 2H), 7.56 (d, J=0.7 Hz, 1H), 7.72 (d, J=0.7 Hz, 1H)

Example 8

4-((1-methylpyrrol-2-yl)-carbonyl)-N-(4-(4-(2-(1,2,4-triazol-1-yl)-ethyl)piperidin-1-yl)-phenyl)-1-piperazinecarboxamide Example 8(1)

4-[2-(1,2,4-triazol-1-yl)-ethyl]-N-(4-nitrophenyl)piperidine

Following the procedure of Example 6(3), 1,2,4-triazole was used instead of morpholine, thereby obtaining 4-[2-(1,2,4-triazol-1-yl)-ethyl]-N-(4-nitrophenyl)piperidine (78%) as a yellow solid.

1H-NMR (CDCl3): δ (ppm) 1.23-1.65 (m, 3H), 1.74-2.03 (m, 4H), 2.82-3.09 (m, 2H), 3.85-4.08 (m, 2H), 4.26 (t, J=7.1 Hz, 2H), 6.80 (d, J=9.4 Hz, 2H), 7.95 (s, 1H), 8.08 (s, 1H), 8.10 (d, J=9.4 Hz, 2H)

Example 8(2)

4-[2-(1,2,4-triazol-1-yl)-ethyl]-N-(4-aminophenyl)piperidine

Following the procedure of Example 1(2), the 4-[2-(1,2,4-triazol-1-yl)-ethyl]-N-(4-nitrophenyl)piperidine obtained in Example 8(1) was used instead of 4-hydroxy-N-(4-nitrophenyl)piperidine, thereby obtaining 4-[2-(1,2,4-triazol-1-yl)-ethyl]-N-(4-aminophenyl)piperidine (99%) as a reddish-purple solid.

1H-NMR (CDCl3): δ (ppm) 1.20-1.55 (m, 3H), 1.66-1.90 (m, 4H), 2.43-2.64 (m, 2H), 3.27-3.44 (m, 2H), 3.45-4.05 (br, 2H), 4.16 (t, J=7.3 Hz, 2H), 6.55 (d, J=8.6 Hz, 2H), 6.77 (d, J=8.6 Hz, 2H), 7.85 (s, 1H), 8.01 (s, 1H)

Example 8(3)

4-((1-methylpyrrol-2-yl)-carbonyl)-N-(4-(4-(2-(1,2,4-triazol-1-yl)-ethyl)piperidin-1-yl)-phenyl)-1-piperazinecarboxamide Following the procedure of Example 1(3), the 4-[2-(1,2,4-triazol-1-yl)-ethyl]-N-(4-aminophenyl)piperidine obtained in Example 8(2) was used instead of 4-hydroxy-N-(4-aminophenyl)piperidine, thereby obtaining 4-((1-methylpyrrol-2-yl)-carbonyl)-N-(4-(4-(2-(1,2,4-triazol-1-yl)-ethyl)piperidin-1-yl)-phenyl)-1-piperazinecarboxamide (45%) as a milky-white solid.

1H-NMR (CDCl3): δ (ppm) 1.30-1.98 (m, 7H), 2.53-2.75 (m, 2H), 3.43-3.67 (m, 6H), 3.71-3.92 (m, 4H), 3.80 (s, 3H), 4.25 (t, J=7.3 Hz, 2H), 6.07-6.15 (m, 1H), 6.27 (brs, 1H), 6.29-6.42 (m, 1H), 6.67-6.74 (m, 1H), 6.88 (d, J=9.0 Hz, 2H), 7.21 (d, J=9.0 Hz, 2H), 7.95 (s, 1H), 8.07 (s, 1H)

Example 9

4-((1-methylpyrrol-2-yl)-carbonyl)-N-(4-(4-(2-(3,5-dimethyl-1,2,4-triazol-1-yl)-ethyl)piperidin-1-yl)-phenyl)-1-piperazinecarboxamide Example 9(1)

4-[2-(3,5-dimethyl-1,2,4-triazol-1-yl)-ethyl]-N-(4-nitrophenyl)piperidine

Following the procedure of Example 6(3), 3,5-dimethyl-1,2,4-triazole was used instead of morpholine, thereby obtaining 4-[2-(3,5-dimethyl-1,2,4-triazol-1-yl)-ethyl]-N-(4-nitrophenyl)piperidine (84%) as a yellow solid.

1H-NMR (CDCl3): δ (ppm) 1.25-1.90 (m, 7H), 2.33 (s, 3H), 2.41 (s, 3H), 2.86-3.05 (m, 2H), 3.88-4.10 (m, 4H), 6.80 (d, J=9.4 Hz, 2H), 8.10 (d, J=9.4 Hz, 2H)

Example 9(2)

4-[2-(3,5-dimethyl-1,2,4-triazol-1-yl)-ethyl]-N-(4-aminophenyl)piperidine

Following the procedure of Example 1(2), the 4-[2-(3,5-dimethyl-1,2,4-triazol-1-yl)-ethyl]-N-(4-nitrophenyl)piperidine obtained in Example 9(1) was used instead of 4-hydroxy-N-(4-nitrophenyl)piperidine, thereby obtaining 4-[2-(3,5-dimethyl-1,2,4-triazol-1-yl)ethyl]-N-(4-aminophenyl)piperidine (97%) as a reddish-purple solid.

1H-NMR (CDCl3): δ (ppm) 1.28-1.55 (m, 3H), 1.62-1.89 (m, 4H), 2.33 (s, 3H), 2.40 (s, 3H), 2.47-2.66 (m, 2H), 3.10-3.60 (m, 4H), 3.98-4.10 (m, 2H), 6.64 (d, J=8.7 Hz, 2H), 6.81 (d, J=8.7 Hz, 2H)

Example 9(3)

4-((1-methylpyrrol-2-yl)-carbonyl)-N-(4-(4-(2-(3,5-dimethyl-1,2,4-triazol-1-yl-ethyl)piperidin-1-yl)-phenyl)-1-piperazinecarboxamide Following the procedure of Example 1(3), the 4-[2-(3,5-dimethyl-1,2,4-triazol-1-yl)-ethyl]-N-(4-aminophenyl)piperidine obtained in Example 9(2) was used instead of 4-hydroxy-N-(4-aminophenyl)piperidine, thereby obtaining 4-((1-methylpyrrol-2-yl) carbonyl)-N-(4-(4-(2-(3,5-dimethyl-1,2,4-triazol-1-yl)-ethyl)piperidin-1-yl)-phenyl)-1-piperazinecarboxamide (76%) as a white solid.

1H-NMR (CDCl3): δ (ppm) 1.30-1.55 (m, 3H), 1.72-1.95 (m, 4H), 2.33 (s, 3H), 2.40 (s, 3H), 2.57-2.75 (m, 2H), 3.48-3.65 (m, 6H), 3.73-3.90 (m, 4H), 3.80 (s, 3H), 4.03 (t, J=7.5 Hz, 2H), 6.06-6.13 (m, 1H), 6.31-6.38 (m, 1H), 6.40 (brs, 1H), 6.68-6.74 (m, 1H), 6.88 (d, J=9.1 Hz, 2H), 7.21 (d, J=9.1 Hz, 2H)

Example 10

4-((1-methylpyrrol-2-yl)-carbonyl)-N-(4-(4-(2-(pyrazol-1-yl)-ethyl)piperidin-1-yl)-phenyl)-1-piperazinecarboxamide Example 10(1)

4-[2-(pyrazol-1-yl)-ethyl]-N-(4-nitrophenyl)piperidine

Following the procedure of Example 6(3), pyrazole was used instead of morpholine, thereby obtaining 4-[2-(pyrazol-1-yl)-ethyl]-N-(4-nitrophenyl)piperidine (72%) as a yellow solid.

1H-NMR (CDCl3): δ (ppm) 1.23-1.67 (m, 3H), 1.76-1.98 (m, 4H), 2.84-3.05 (m, 2H), 3.85-4.03 (m, 2H), 4.21 (t, J=7.1 Hz, 2H), 6.21-6.34 (m, 1H), 6.79 (d, J=9.4 Hz, 2H), 7.36-7.45 (m, 1H), 7.48-7.57 (m, 1H), 8.10 (d, J=9.4 Hz, 2H)

Example 10(2)

4-[2-(pyrazol-1-yl)-ethyl]-N-(4-aminophenyl)piperidine

Following the procedure of Example 1(2), the 4-[2-(pyrazol-1-yl)-ethyl]-N-(4-nitrophenyl)piperidine obtained in Example 10(1) was used instead of 4-hydroxy-N-(4-nitrophenyl)piperidine, thereby obtaining 4-[2-(pyrazol-1-yl)-ethyl]-N-(4-aminophenyl)piperidine (83%) as a reddish-purple solid.

1H-NMR (CDCl3): δ (ppm) 1.25-1.64 (m, 3H), 1.73-1.96 (m, 4H), 2.51-2.70 (m, 2H), 3.38-3.53 (m, 2H), 4.10-2.70 (br, 2H), 4.20 (t, J=7.3 Hz, 2H), 6.25 (t, J=1.8 Hz, 1H), 6.64 (d, J=8.7 Hz, 2H), 6.86 (d, J=8.7 Hz, 2H), 7.39 (d, J=1.8 Hz, 1H), 7.50 (d, J=1.8 Hz, 1H)

Example 10(3)

4-((1-methylpyrrol-2-yl)-carbonyl)-N-(4-(4-(2-(pyrazol-1-yl)-ethyl)piperidin-1-yl)-phenyl)-1-piperazinecarboxamide Following the procedure of Example 1(3), the 4-[2-(pyrazol-1-yl)-ethyl]-N-(4-aminophenyl)piperidine obtained in Example 10(2) was used instead of 4-hydroxy-N-(4-aminophenyl)piperidine, thereby obtaining 4-((1-methylpyrrol-2-yl)-carbonyl)-N-(4-(4-(2-(pyrazol-1-yl)-ethyl)piperidin-1-yl)-phenyl)-1-piperazinecarboxamide (56%) as a milky-white solid.

1H-NMR (CDCl3): δ (ppm) 1.30-1.52 (m, 3H), 1.70-1.97 (m, 4H), 2.53-2.74 (m, 2H), 3.45-3.67 (m, 6H), 3.71-3.93 (m, 4H), 3.80 (s, 3H), 4.20 (t, J=7.3 Hz, 2H), 6.06-6.18 (m, 1H), 6.22-6.40 (m, 3H), 6.67-6.78 (m, 1H), 6.88 (d, J=9.0 Hz, 2H), 7.20 (d, J=9.0 Hz, 2H), 7.39 (d, J=2.3 Hz, 1H), 7.51 (d, J=1.6 Hz, 1H)

Example 11

4-((1-methylpyrrol-2-yl)-carbonyl)-N-(4-(4-(3-(1,2,4-triazol-1-yl-propyl)piperidin-1-yl)-phenyl)-1-piperazinecarboxamide

Example 11(1)

4-hydroxypropyl-N-(4-nitrophenyl)piperidine

Following the procedure of Example 1(1), 4-hydroxypropylpiperidine was used instead of 4-hydroxypiperidine, thereby obtaining 4-hydroxypropyl-N-(4-nitrophenyl)piperidine (46%) as a yellow solid.

1H-NMR (CDCl3): δ (ppm) 1.19-1.97 (m, 10H), 2.85-3.08 (m, 2H), 3.57-3.76 (m, 2H), 3.88-4.05 (m, 2H), 6.79 (d, J=9.6 Hz, 2H), 8.10 (d, J=9.6 Hz, 2H)

Example 11(2)

4-tosyloxypropyl-N-(4-nitrophenyl)piperidine

Following the procedure of Example 4(2), the 4-hydroxypropyl-N-(4-nitrophenyl)piperidine obtained in Example 11(1) was used instead of 4-hydroxymethyl-N-(4-nitrophenyl)piperidine, thereby obtaining 4-tosyloxypropyl-N-(4-nitrophenyl)piperidine (97%) as a yellow solid.

1H-NMR (CDCl3): δ (ppm) 1.15-1.84 (m, 9H), 2.45 (s, 3H), 2.82-3.03 (m, 2H), 3.84-4.00 (m, 2H), 4.04 (t, J=6.3 Hz, 2H), 6.78 (d, J=9.6 Hz, 2H), 7.35 (d, J=7.9 Hz, 2H), 7.79 (d, J=7.9 Hz, 2H), 8.10 (d, J=9.6 Hz, 2H)

Example 11(3)

4-[3-(1,2,4-triazol-1-yl)-propyl]-N-(4-nitrophenyl)piperidine

The 4-tosyloxypropyl-N-(4-nitrophenyl)piperidine (4.19 g, 10.0 mmol) obtained in Example 11(2) was dissolved in acetonitrile (40 ml), and potassium carbonate (2.76 g, 20 mmol) and 1,2,4-triazole (1.04 g, 15.0 mmol) were added thereto, followed by stirring at 80° C. for 18 hours. After the reaction mixture was allowed to cool to room temperature, ethyl acetate was added to the reaction mixture, and the organic layer was washed with water and saturated sodium chloride, and dried over anhydrous sodium sulfate. After the desiccant was filtered off, the residue obtained by evaporation under reduced pressure was purified using medium pressure silica gel flash column chromatography (methanol:chloroform=1:100 to 1:30), thereby obtaining 4-[3-(1,2,4-triazol-1-yl)-propyl]-N-(4-nitrophenyl)piperidine (2.47 g, 78%) as a yellow solid.

1H-NMR (CDCl3): δ (ppm) 1.17-1.39 (m, 4H), 1.45-1.65 (m, 1H), 1.70-2.05 (m, 4H), 2.83-3.05 (m, 2H), 3.84-4.02 (m, 2H), 4.18 (t, J=7.1 Hz, 2H), 6.79 (d, J=9.6 Hz, 2H), 7.95 (s, 1H), 8.05 (s, 1H), 8.10 (d, J=9.6 Hz, 2H)

Example 11(4)

4-[3-(1,2,4-triazol-1-yl)-propyl]-N-(4-aminophenyl)piperidine

Following the procedure of Example 1(2), the 4-[3-(1,2,4-triazol-1-yl)-propyl]-N-(4-nitrophenyl)piperidine obtained in Example 11(3) was used instead of 4-hydroxy-N-(4-nitrophenyl)piperidine, thereby obtaining 4-[3-(1,2,4-triazol-1-yl)-propyl]-N-(4-aminophenyl)piperidine (95%) as a reddish-purple solid.

1H-NMR (CDCl3): δ (ppm) 1.20-1.48 (m, 5H), 1.65-2.07 (m, 4H), 2.43-2.68 (m, 2H), 3.06-3.77 (m, 4H), 4.17 (t, J=7.1 Hz, 2H), 6.63 (d, J=8.9 Hz, 2H), 6.82 (d, J=8.9 Hz, 2H), 7.94 (s, 1H), 8.05 (s, 1H)

Example 11(5)

4-((1-methylpyrrol-2-yl)-carbonyl)-N-(4-(4-(3-(1,2,4-triazol-1-yl-propyl)piperidin-1-yl)-phenyl)piperazinecarboxamide Following the procedure of Example 1(3), the 4-[3-(1,2,4-triazol-1-yl)-propyl]-N-(4-aminophenyl)piperidine obtained in Example 11(4) was used instead of 4-hydroxy-N-(4-aminophenyl)piperidine, thereby obtaining 4-((1-methylpyrrol-2-yl)-carbonyl)-N-(4-(4-(3-(1,2,4-triazol-1-yl-propyl)piperidin-1-yl)-phenyl)piperazinecarboxamide (67%) as a milky-white solid.

1H-NMR (CDCl3): δ (ppm) 1.20-1.48 (m, 5H), 1.66-2.05 (m, 4H), 2.52-2.74 (m, 2H), 3.44-3.65 (m, 6H), 3.80 (s, 3H), 3.75-3.92 (m, 4H), 4.17 (t, J=7.1 Hz, 2H), 6.05-6.14 (m, 1H), 6.31 (brs, 1H), 6.30-6.44 (m, 1H), 6.67-6.79 (m, 1H), 6.88, (d, J=9.1 Hz, 2H), 7.20 (d, J=9.1 Hz, 2H), 7.95 (s, 1H), 8.05 (s, 1H)

Example 12

4-((1-methylpyrrol-2-yl)-carbonyl)-N-(4-(4-(3-(1,2,3-triazol-1-yl)-propyl)piperidin-1-yl)-phenyl)-1-piperazinecarboxamide

Example 12(1)

4-[3-(1,2,3-triazol-1-yl)-propyl]-N-(4-nitrophenyl)piperidine

Following the procedure of Example 7(1), the 4-tosyloxypropyl-N-(4-nitrophenyl)piperidine obtained in Example 11(2) was used instead of 4-tosyloxyethyl-N-(4-nitrophenyl)piperidine, thereby obtaining 4-[2-(1,2,3-triazol-1-yl)-propyl]-N-(4-aminophenyl)piperidine (69%) as a yellow solid.

1H-NMR (CDCl3): δ (ppm) 1.16-1.40 (m, 4H), 1.48-1.67 (m, 1H), 1.70-2.09 (m, 4H), 2.83-3.05 (m, 2H), 3.85-4.03 (m, 2H), 4.40 (t, J=7.1 Hz, 2H), 6.79 (d, J=9.6 Hz, 2H), 7.54 (d, J=0.9 Hz, 1H), 7.71 (d, J=0.9 Hz, 1H), 8.10 (d, J=9.6 Hz, 2H)

Example 12(2)

4-[2-(1,2,3-triazol-1-yl)-propyl]-N-(4-aminophenyl) piperidine

Following the procedure of Example 1(2), the 4-[2-(1,2,3-triazol-1-yl)-propyl]-N-(4-nitrophenyl)piperidine obtained in Example 12(1) was used instead of 4-hydroxy-N-(4-nitrophenyl)piperidine, thereby obtaining 4-[2-(1,2,3-triazol-1-yl)-propyl]-N-(4-aminophenyl)piperidine (94%) as a reddish-purple solid.

1H-NMR (CDCl3): δ (ppm) 1.23-1.46 (m, 5H), 1.59-1.87 (m, 2H), 1.90-2.05 (m, 2H), 2.45-2.63 (m, 2H), 3.30-3.52 (m, 4H), 4.40 (t, J=7.2 Hz, 2H), 6.64 (d, J=8.8 Hz, 2H), 6.81 (d, J=8.8 Hz, 2H), 7.53 (d, J=0.7 Hz, 1H), 7.71 (d, J=0.7 Hz, 1H)

Example 12(3)

4-((1-methylpyrrol-2-yl)-carbonyl)-N-(4-(4-(3-(1,2,3-triazol-1-yl)-propyl)piperidin-1-yl)-phenyl)-1-piperazinecarboxamide Following the procedure of Example 1(3), the 4-[2-(1,2,3-triazol-1-yl)-propyl]-N-(4-aminophenyl)piperidine obtained in Example 12(2) was used instead of 4-hydroxy-N-(4-aminophenyl)piperidine, thereby obtaining 4-((1-methylpyrrol-2-yl)-carbonyl)-N-(4-(4-(3-(1,2,3-triazol-1-yl)-propyl)piperidin-1-yl)-phenyl)-1-piperazinecarboxamide (57%) as a milky-white solid.

1H-NMR (CDCl3): δ (ppm) 1.22-1.48 (m, 5H), 1.68-2.08 (m, 4H), 2.50-2.72 (m, 2H), 3.45-3.66 (m, 6H), 3.80 (s, 3H), 3.73-3.90 (m, 4H), 4.39 (t, J=7.1 Hz, 2H), 6.07-6.14 (m, 1H), 6.30-6.45 (m, 2H), 6.68-6.77 (m, 1H), 6.87 (d, J=8.9 Hz, 2H), 7.21 (d, J=8.9 Hz, 2H), 7.55 (d, J=0.8 Hz, 1H), 7.71 (d, J=0.8 Hz, 1H)

Example 13

4-((1-ethylpyrrol-2-yl)-carbonyl)-N-(4-(4-morpholin-1-yl-carbonylpiperidin-1-yl)-phenyl)-1-piperazinecarboxamide Example 13(1)

4-(benzyloxycarbonyl)-N-(4-(4-morpholin-1-yl-carbonylpiperidin-1-yl)-phenyl)-1-piperazinecarboxamide 4-nitrophenyl chloroformate (7.26 g, 36.0 mmol) was dissolved in tetrahydrofuran (100 ml), and a tetrahydrofuran (50 ml) solution of the 1-(4-aminophenyl)piperidine-4-morpholinecarboxamide (8.68 g, 30.0 mmol) obtained in Example 3(3) was added dropwise at −30° C. After stirring for 30 minutes at the same temperature, a tetrahydrofuran (30 ml) solution of N-benzyloxycarbonylpiperazine (7.27 g, 33.0 mmol) and triethylamine (14.0 ml, 100 mmol) were added to the mixture, followed by stirring at room temperature for 13 hours and further at 60° C. for 4 hours. After the reaction mixture was cooled to room temperature, a dilute sodium hydroxide aqueous solution was added thereto, followed by extraction with ethyl acetate. The organic layer was washed with water and saturated sodium chloride, and dried over anhydrous sodium sulfate. After the desiccant was filtered off, the residue obtained by evaporation under reduced pressure was purified using medium pressure silica gel flash column chromatography (silica gel, methanol:chloroform=0:1 to 1:30), thereby obtaining 4-(benzyloxycarbonyl)-N-(4-(4-morpholin-1-yl-carbonylpiperidin-1-yl)-phenyl)-1-piperazinecarboxamide (9.02 g, 56%) as a milky-white solid.

1H-NMR (CDCl3): δ (ppm) 1.72-1.87 (m, 2H), 1.90-2.12 (m, 2H), 2.47-2.78 (m, 3H), 3.38-3.77 (m, 18H), 5.16 (s, 2H), 6.24 (s, 1H), 6.88 (d, J=8.9 Hz, 2H), 7.20 (d, J=8.9 Hz, 2H), 7.29-7.44 (m, 5H)

Example 13(2)

N-(4-(4-morpholin-1-yl-carbonylpiperidin-1-yl)-phenyl)-1-piperazinecarboxamide

The 4-(benzyloxycarbonyl)-N-(4-(4-morpholin-1-yl-carbonylpiperidin-1-yl)-phenyl)-1-piperazinecarboxamide (5.89 g, 11.0 mmol) obtained in Example 13(1) was suspended in tetrahydrofuran (80 ml) and methanol (80 ml), and 10% palladium-carbon (1.5 g) was added thereto, followed by stirring at room temperature in an atmosphere of hydrogen gas for 18 hours. After the insoluble material was filtered with Celite, the filtrate was concentrated under reduced pressure, and the obtained residue was purified using medium pressure silica gel flash column chromatography (NH silica gel, methanol:chloroform=1:50 to 1:15), thereby obtaining N-(4-(4-morpholin-1-yl-carbonylpiperidin-1-yl)-phenyl)-1-piperazinecarboxamide (3.62 g, 82%) as a milky-white solid.

1H-NMR (CDCl3): δ (ppm) 1.73-1.86 (m, 2H), 1.90-2.10 (m, 2H), 2.48-2.76 (m, 3H), 2.83-3.00 (m, 4H), 3.35-3.78 (m, 15H), 6.22 (s, 1H), 6.88 (d, J=9.1 Hz, 2H), 7.22 (d, J=9.1 Hz, 2H)

Example 13(3)

4-((1-ethylpyrrol-2-yl)-carbonyl)-N-(4-(4-morpholin-1-yl-carbonylpiperidin-1-yl)-phenyl)-1-piperazinecarboxamide 1-ethylpyrrole-2-carboxylic acid (153 mg, 1.1 mmol) was dissolved in N,N-dimethylformamide (3.0 ml), and 1-ethyl-3-(3-dimethylaminopropyl)carbodiimide hydrochloride (253 mg, 1.3 mmol), 1-hydroxybenzotriazole monohydrate (185 mg, 1.2 mmol), and the N-(4-(4-morpholin-1-yl-carbonylpiperidin-1-yl)-phenyl)-1-piperazinecarboxamide (201 mg, 0.5 mica) obtained in Example 13(2) were added thereto, followed by stirring under heat at 60° C. for 15 hours. After the reaction mixture was allowed to cool to room temperature, a saturated sodium bicarbonate aqueous solution was added to the reaction mixture, followed by extraction with chloroform. The extract was washed with water and saturated sodium chloride, and dried over anhydrous sodium sulfate. After the desiccant was filtered off, the residue obtained by evaporation under reduced pressure was purified using medium pressure silica gel flash column chromatography (methanol:chloroform=1:50 to 1:30), thereby obtaining 4-((1-ethylpyrrol-2-yl)-carbonyl)-N-(4-(4-morpholin-1-yl-carbonylpiperidin-1-yl)-phenyl)-1-piperazinecarboxamide (228 mg, 44%) as a milky-white solid.

1H-NMR (CDCl3): δ (ppm) 1.38 (t, J=7.3 Hz, 3H), 1.72-2.10 (m, 4H), 2.48-2.80 (m, 3H), 3.40-3.92 (m, 18H), 4.18 (q, J=7.3 Hz, 2H), 6.08-6.17 (m, 1H), 6.28-6.40 (m, 1H), 6.37 (brs, 1H), 6.75-6.83 (m, 1H), 6.89 (d, J=8.9 Hz, 2H), 7.22 (d, J=8.9 Hz, 2H)

Example 14

4-((1-methylpyrrol-2-yl)-carbonyl)-N-(4-(4-piperidin-1-yl-carbonylpiperidin-1-yl)-phenyl)-1-piperazinecarboxamide The 4-(((((1-methylpyrrol-2-yl)-carbonyl)-1-piperazinyl)-carbonyl)amino-4-phenylpiperidine-4-carboxylic acid (440 mg, 1.0 mmol) obtained in Example 2(4) was dissolved in N,N-dimethylformamide (3 ml), and 1-ethyl-3-(3-dimethylaminopropyl)carbodiimide hydrochloride (230 mg, 1.2 mmol), 1-hydroxybenzotriazole monohydrate (168 mg, 1.1 mmol), and piperidine (0.12 ml, 1.2 mmol) were added thereto, followed by stirring under heat at 60° C. for 6 hours. After the reaction mixture was cooled to room temperature, a saturated sodium bicarbonate aqueous solution was added thereto, followed by extraction with ethyl acetate. The organic layer was washed with water and saturated sodium chloride, and dried over anhydrous sodium sulfate. After the desiccant was filtered off, the residue obtained by evaporation under reduced pressure was purified using medium pressure silica gel flash column chromatography (methanol:chloroform=1:50 to 1:20), thereby obtaining 4-((1-methylpyrrol-2-yl)-carbonyl)-N-(4-(4-piperidin-1-yl-carbonylpiperidin-1-yl)-phenyl)-1-piperazinecarboxamide (226 mg, 45%) as a milky-white solid.

1H-NMR (CDCl3): δ (ppm) 1.58-1.67 (m, 6H), 1.77-2.00 (m, 4H), 2.54-2.74 (m, 3H), 3.34-3.93 (m, 17H), 6.05-6.15 (m, 1H), 6.32-6.50 (m, 2H), 6.68-6.77 (m, 1H), 6.89 (d, J=8.9 Hz, 2H), 7.21 (d, J=8.9 Hz, 2H)

Example 15

4-((1-methylpyrrol-2-yl)-carbonyl)-N-(4-(4-(4-methylpiperazin-1-yl-carbonyl)piperidin-1-yl)-phenyl)-1-piperazinecarboxamide Following the procedure of Example 14, 1-methylpiperazine was used instead of piperidine, thereby obtaining 4-((1-methylpyrrol-2-yl)-carbonyl)-N-(4-(4-(4-methylpiperazin-1-yl-carbonyl)piperidin-1-yl)-phenyl)-1-piperazinecarboxamide (14%) as a milky-white solid.

1H-NMR (CDCl3): δ (ppm) 1.63-2.15 (m, 4H), 2.30-2.77 (m, 10H), 3.52-3.93 (m, 17H), 6.08-6.15 (m, 1H), 6.30-6.45 (m, 2H), 6.68-6.75 (m, 1H), 6.88 (d, J=8.7 Hz, 2H), 7.22 (d, J=8.7 Hz, 2H)

Example 16

4-((1-methylpyrrol-2-yl)-carbonyl)-N-(4-(4-(2-morpholinoethylcarbamoyl)piperidin-1-yl)-phenyl)-1-piperazinecarboxamide Following the procedure of Example 14, 2-aminoethylmorpholine was used instead of piperidine, thereby obtaining 4-((1-methylpyrrol-2-yl)-carbonyl)-N-(4-(4-(2-morpholinoethylcarbamoyl)piperidin-1-yl)-phenyl)-1-piperazinecarboxamide (38%) as a pale yellow solid.

1H-NMR (CDCl3): δ (ppm) 1.75-2.03 (m, 4H), 2.14-2.29 (m, 1H), 2.34-2.55 (m, 6H), 2.62-2.78 (m, 2H), 3.28-3.41 (m, 2H), 3.49-3.87 (m, 17H), 6.02-6.18 (m, 2H), 6.31-6.40 (m, 1H), 6.43 (s, 1H), 6.67-6.75 (m, 1H), 6.88 (d, J=8.8 Hz, 2H), 7.22 (d, J=8.8 Hz, 2H)

Example 17

4-((1-methylpyrrol-2-yl)-carbonyl)-N-(4-(4-(pyridin-3-ylmethylcarbamoyl)piperidin-1-yl)-phenyl)-1-piperazinecarboxamide Following the procedure of Example 14, 3-aminomethylpyridine was used instead of piperidine, thereby obtaining 4-((1-methylpyrrol-2-yl)-carbonyl)-N-(4-(4-(pyridin-3-ylmethylcarbamoyl)piperidin-1-yl)-phenyl)-1-piperazinecarboxamide (33%) as a milky-white solid.

1H-NMR (CDCl3): δ (ppm) 1.76-1.99 (m, 4H), 2.13-2.34 (m, 1H), 2.55-2.74 (m, 2H), 3.44-3.88 (m, 13H), 4.44 (d, J=5.9 Hz, 2H), 6.10 (dd, J=2.7, 3.8 Hz, 1H), 6.25-6.40 (m, 2H), 6.56 (s, 1H), 6.69-6.76 (m, 1H), 6.84 (d, J=8.9 Hz, 2H), 7.13-7.34 (m, 3H), 7.55-7.67 (m, 1H), 8.45-8.60 (m, 2H)

REFERENCE EXAMPLES

Method A

Following the procedure of Example 13(3), corresponding carboxylic acid was used instead of 1-ethylpyrrole-2-carboxylic acid, thereby obtaining the title compound.

Method B

The N-(4-(4-morpholin-1-yl-carbonylpiperidin-1-yl)-phenyl)-1-piperazinecarboxamide obtained in Example 13(2) was suspended in tetrahydrofuran and chloroform, and triethylamine and corresponding acid chloride were added thereto, followed by stirring at room temperature. A saturated sodium bicarbonate aqueous solution was added to the reaction mixture, followed by extraction with chloroform. The extract was washed with water and saturated sodium chloride, and dried over anhydrous sodium sulfate. After the desiccant was filtered off, the residue obtained by evaporation under reduced pressure was purified using medium pressure silica gel flash column chromatography, thereby obtaining the title compound.

Reference Example 1

4-((pyrrol-2-yl)-carbonyl)-N-(4-(4-morpholin-1-yl-carbonylpiperidin-1-yl)-phenyl)-1-piperazinecarboxamide Method A, yield: 53%

1H-NMR (CDCl3): δ (ppm) 1.72-2.13 (m, 4H), 2.49-2.80 (m, 3H), 3.46-4.08 (m, 18H), 6.23-6.32 (m, 1H), 6.33 (brs, 1H), 6.50-6.63 (m, 1H), 6.89 (d, J=8.9 Hz, 2H), 6.90-7.05 (m, 1H), 7.23 (d, J=8.9 Hz, 2H), 9.50 (brs, 1H)

Reference Example 2

4-((3,5-dimethylpyrrol-2-yl)-carbonyl)-N-(4-(4-morpholin-1-yl-carbonylpiperidin-1-yl)-phenyl)-1-piperazinecarboxamide Method A, yield: 25%

1H-NMR (CDCl3): δ (ppm) 1.60-2.15 (m, 4H), 2.11 (s, 3H), 2.23 (s, 3H), 2.47-2.79 (m, 3H), 3.40-3.82 (m, 18H), 5.74 (d, J=2.6 Hz, 1H), 6.37-6.54 (m, 1H), 6.88 (d, J=8.9 Hz, 2H), 7.21 (d, J=8.9 Hz, 2H), 8.63 (brs, 1H)

Reference Example 3

4-((1-methylpyrrol-3-yl)-carbonyl)-N-(4-(4-morpholin-1-yl-carbonylpiperidin-1-yl)-phenyl)-1-piperazinecarboxamide Method A, yield: 42%
1H-NMR (CDCl3): δ (ppm) 1.65-2.12 (m, 4H), 2.47-2.80 (m, 3H), 3.45-3.87 (m, 18H), 3.67 (s, 3H), 6.24-6.32 (m, 1H), 6.47 (brs, 1H), 6.53-6.62 (m, 1H), 6.88 (d, J=8.9 Hz, 2H), 6.98-7.05 (m, 1H), 7.22 (d, J=8.9 Hz, 2H)

Reference Example 4

4-((thiophen-2-yl)-carbonyl)-N-(4-(4-morpholin-1-yl-carbonylpiperidin-1-yl)-phenyl)-1-piperazinecarboxamide Method A, yield: 54%
1H-NMR (CDCl3): δ (ppm) 1.70-2.10 (m, 4H), 2.45-2.80 (m, 3H), 3.43-3.91 (m, 18H), 6.37 (brs, 1H), 6.89 (d, J=8.9 Hz, 2H), 7.02-7.13 (m, 1H), 7.22 (d, J=8.9 Hz, 2H), 7.25-7.37 (m, 1H), 7.40-7.54 (m, 1H)

Reference Example 5

4-((thiophen-3-yl)-carbonyl)-N-(4-(4-morpholin-1-yl-carbonylpiperidin-1-yl)-phenyl)-1-piperazinecarboxamide Method B, yield: 70%
1H-NMR (CDCl3): δ (ppm) 1.72-2.10 (m, 4H), 2.48-2.80 (m, 3H), 3.38-3.89 (m, 18H), 6.44 (brs, 1H), 6.88 (d, J=8.9 Hz, 2H), 7.15-7.27 (m, 3H), 7.37 (dd, J=4.9, 3.0 Hz, 1H), 7.55 (dd, J=3.0, 1.3 Hz, 1H)

Reference Example 6

4-((furan-2-yl)-carbonyl)-N-(4-(4-morpholin-1-yl-carbonylpiperidin-1-yl)-phenyl)-1-piperazinecarboxamide Method B, yield: 76%
1H-NMR (CDCl3): δ (ppm) 1.71-2.10 (m, 4H), 2.48-2.81 (m, 3H), 3.45-4.00 (m, 18H), 6.34-6.46 (m, 1H), 6.51 (dd, J=3.5, 1.8 Hz, 1H), 6.89 (d, J=8.9 Hz, 2H), 7.06 (dd, J=3.5, 0.8 Hz, 1H), 7.22 (d, J=8.9 Hz, 2H), 7.51 (dd, J=1.8, 0.8 Hz, 1H)

Reference Example 7

4-((furan-3-yl)-carbonyl)-N-(4-(4-morpholin-1-yl-carbonylpiperidin-1-yl)-phenyl)-1-piperazinecarboxamide Method A, yield: 58%
1H-NMR (CDCl3): δ (ppm) 1.73-2.07 (m, 4H), 2.50-2.84 (m, 3H), 3.47-3.85 (m, 18H), 6.53-6.62 (m, 1H), 6.87 (d, J=8.9 Hz, 2H), 7.29 (d, J=8.9 Hz, 2H), 7.45-7.53 (m, 1H), 7.70-7.78 (m, 1H), 7.85 (brs, 1H)

Reference Example 8

4-((isoxazol-5-yl)-carbonyl)-N-(4-(4-morpholin-1-yl-carbonylpiperidin-1-yl)-phenyl)-1-piperazinecarboxamide Method B, yield: 56%
1H-NMR (CDCl3): δ (ppm) 1.72-2.09 (m, 4H), 2.49-2.78 (m, 3H), 3.48-3.90 (m, 18H), 6.37 (brs, 1H), 6.84 (d, J=1.8 Hz, 1H), 6.89 (d, J=9.1 Hz, 2H), 7.21 (d, J=9.1 Hz, 2H), 8.34 (d, J=1.8 Hz, 1H)

Reference Example 9

4-((1-methylimidazol-2-yl)-carbonyl)-N-(4-(4-morpholin-1-yl-carbonylpiperidin-1-yl)-phenyl)-1-piperazinecarboxamide Method A, yield: 27%
1H-NMR (CDCl3): δ (ppm) 1.73-2.10 (m, 4H), 2.47-2.80 (m, 3H), 3.47-3.88 (m, 16H), 3.91 (s, 3H), 4.14-4.34 (m, 2H), 6.27 (brs, 1H), 6.89 (d, J=8.9 Hz, 2H), 6.96 (d, J=1.2 Hz, 1H), 7.05 (d, J=1.2 Hz, 1H), 7.22 (d, J=8.9 Hz, 2H)

Reference Example 10

4-(cyclopentylcarbonyl)-N-(4-(4-morpholin-1-yl-carbonylpiperidin-1-yl)-phenyl)-1-piperazinecarboxamide Method B, yield: 84%
1H-NMR (CDCl3): δ (ppm) 1.50-2.11 (m, 12H), 2.47-2.98 (m, 4H), 3.34-3.80 (m, 18H), 6.44 (brs, 1H), 6.88 (d, J=8.9 Hz, 2H), 7.21 (d, J=8.9 Hz, 2H)

Reference Example 11

4-(benzoyl)-N-(4-(4-morpholin-1-yl-carbonylpiperidin-1-yl)-phenyl)-1-piperazinecarboxamide Method B, yield: 69%
1H-NMR (CDCl3): δ (ppm) 1.70-2.10 (m, 4H), 2.47-2.77 (m, 3H), 3.30-3.95 (m, 18H), 6.49 (brs, 1H), 6.87 (d, J=9.1 Hz, 2H), 7.20 (d, J=9.1 Hz, 2H), 7.32-7.50 (m, 5H)

Reference Example 12

4-((1-methylindol-2-yl)-carbonyl)-N-(4-(4-morpholin-1-yl-carbonylpiperidin-1-yl)-phenyl)-1-piperazinecarboxamide Method A, yield: 59%
1H-NMR (CDCl3): δ (ppm) 1.72-2.10 (m, 4H), 2.47-2.79 (m, 3H), 3.47-3.95 (m, 21H), 6.30 (s, 1H), 6.63 (d, J=0.5 Hz, 1H), 6.89 (d, J=8.9 Hz, 2H), 7.11-7.43 (m, 5H), 7.64 (d, J=7.9 Hz, 1H)

Reference Example 13

4-(3-fluorobenzoyl)-piperazine-1-carboxylic acid-(6-bromobenzothiazol-2-yl)amide

Reference Example 14

4-(3-fluorobenzoyl)-piperazine-1-carboxylic acid-(5,6-dimethylbenzothiazol-2-yl)amide

Reference Example 15

4-(3-fluorobenzoyl)piperazine-1-carboxylic acid-(6-methylbenzothiazol-2-yl)amide

Reference Example 16

4-(3-fluorobenzoyl)piperazine-1-carboxylic acid-(6-methoxybenzothiazol-2-yl)amide

Reference Example 17

4-(3-fluorobenzoyl)piperazine-1-carboxylic acid-(6-chlorobenzothiazol-2-yl)amide

Reference Example 18

4-(6-fluoropyridine-2-carbonyl)piperazine-1-carboxylic acid-(4-trifluoromethylphenyl)amide Reference Examples 13 to 18 were synthesized following the procedure of the method disclosed in International Publication WO2008-122787.

Reference Example 19

N-methoxy-N-methyl-4-(5-benzoylbenzimidazol-2-yl)-3,5-dimethylpyrrol-2-carboxamide The synthesis was carried out following the method disclosed in International Publication WO2007-007778.

TEST EXAMPLES

Test Example 1

Hematopoietic Prostaglandin D Synthase (H-PGDS) Inhibiting Action

The test was carried out according to the method of Urade, Y. et al. (J. Biol. Chem., 262, 3820-3825, (1987)). More specifically, the reaction mixture (49 µL) containing 100 mM Tris-HCl (pH 8.0), 1 mM reduced glutathione, 0.1 mg/mL γ-globulin, and human H-PGDS (q.s.), and a compound (final concentration: 0.01-100 µM) was preincubated at 25° C. for 5 minutes. Note that a DMSO solution (final concentration: 1%) was added to the solvent control group. Subsequently, 1 µL of [14C] prostaglandin H2 (final concentration: 10 µM) was added to start the reaction. One minute after the start of the reaction, 250 µL of a reaction stopper solution (diethylether/methanol/1 M citric acid (30/4/1) at a temperature of −20° C. was added to stop the reaction. After the reaction was stopped, 50 µL of the upper layer portion (organic solvent phase) was applied to a TLC plate and developed at −20° C. for 45 minutes (developing solvent: diethylether/methanol/acetic acid (90/2/1)). After drying the TLC plate, the TLC plate was exposed to an imaging plate for 1 to 24 hours, and the radioactivity corresponding to prostaglandin D2 (PGD2) was analyzed using an image analyzer (produced by Fujifilm Corporation). The area (%) occupied by the PGD2 band per lane was calculated to determine the inhibition rate (%) of each Example compound at 0.1 µM relative to the control group in each experiment as well as the inhibition concentration at 50% (IC50 value, nM) relative to H-PGDS. Table 1 shows the results.

TABLE 1

| Compound number | $R^1$ | n | $R^2$ | H-PGDS inhibition rate (%) | IC50 (nM) |
|---|---|---|---|---|---|
| 1 | Me | 2 | HO— | 62.2 | 58 |
| 2 | Me | 2 | HOOC— | 53.7 | 86 |
| 3 | Me | 2 | (acetyl-morpholine) | 54.2 | 76 |

TABLE 1-continued

| | | | | | |
|---|---|---|---|---|---|
| 4 | Me | 2 | 4-ethylmorpholine | 61.5 | 54 |
| 5 | Me | 1 | 1-propyl-1,2,4-triazole | 55.5 | 67 |
| 6 | Me | 2 | 4-propylmorpholine | 68.3 | 43 |
| 7 | Me | 2 | 1-propyl-1,2,3-triazole | 66.7 | 71 |
| 8 | Me | 2 | 1-propyl-1,2,4-triazole | 58.9 | 62 |
| 9 | Me | 2 | 3,5-dimethyl-1-propyl-1,2,4-triazole | 54.8 | 85 |
| 10 | Me | 2 | 1-propylpyrazole | 74.3 | 40 |
| 11 | Me | 2 | 1-butyl-1,2,4-triazole | 71.3 | 46 |
| 12 | Me | 2 | 1-butyl-1,2,3-triazole | 72.7 | 37 |
| 13 | Et | 2 | 4-acetylmorpholine | 51.8 | 91 |
| 14 | Me | 2 | 1-acetylpiperidine | 73.6 | 32 |
| 15 | Me | 2 | 1-acetyl-4-methylpiperazine | 61.3 | 60 |
| 16 | Me | 2 | N-(2-morpholinoethyl)acetamide | 61.1 | 59 |

TABLE 1-continued
| | | | | | |
|---|---|---|---|---|---|
| 17 | Me | 2 | 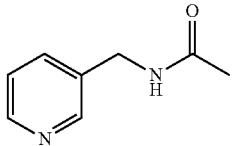 | 61.7 | 60 |
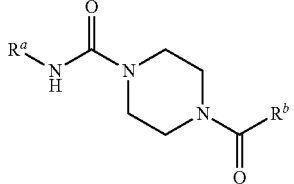
| Compound number | R$^a$ | R$^b$ | H-PGDS inhibition rate (%) | IC50 (nM) |
|---|---|---|---|---|
| Reference Example 1 | 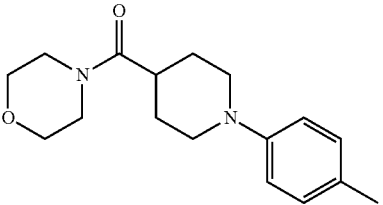 | 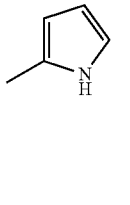 | 2.4 | >1000 |
| Reference Example 2 | 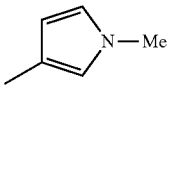 | 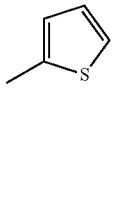 | 3.9 | >1000 |
| Reference Example 3 | 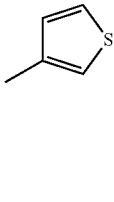 |  | −4.8 | >1000 |
| Reference Example 4 |  |  | 18.0 | 340 |
| Reference Example 5 |  |  | 9.4 | 732 |

TABLE 1-continued
| | | | | |
|---|---|---|---|---|
| Reference Example 6 | 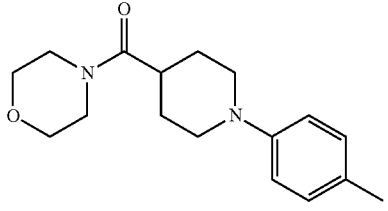 | 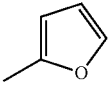 | −2.7 | >1000 |
| Reference Example 7 | 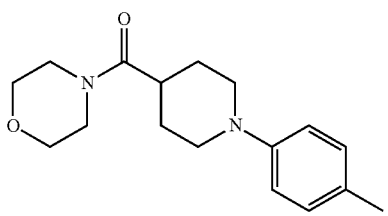 | 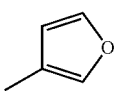 | −4.2 | >1000 |
| Reference Example 8 | 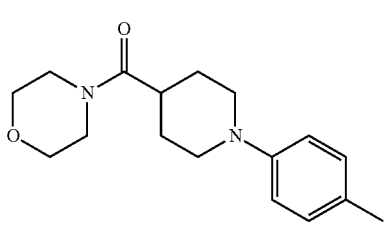 | 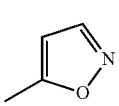 | −6.6 | >1000 |
| Reference Example 9 | 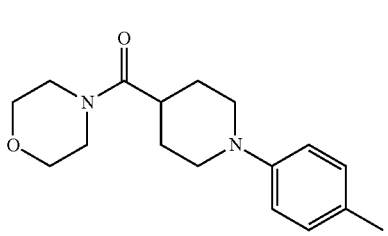 | 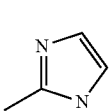 | −2.8 | >1000 |
| Reference Example 10 | 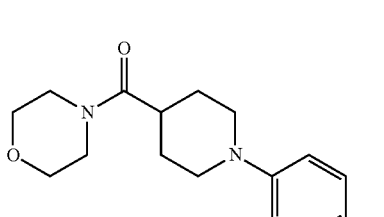 | 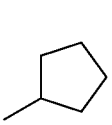 | −2.2 | >1000 |
| Reference Example 11 | 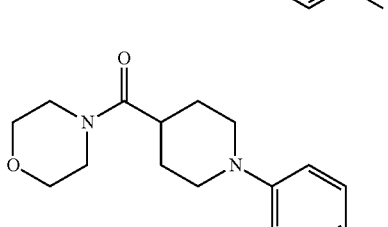 | 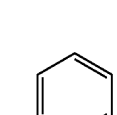 | 15.8 | 437 |
| Reference Example 12 | 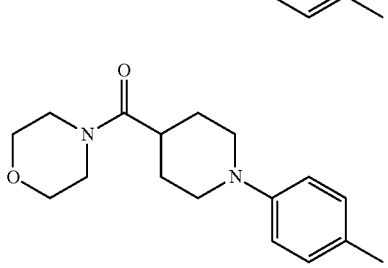 | 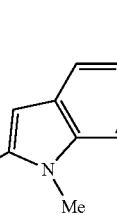 | −0.4 | >1000 |

TABLE 1-continued

| | | | | |
|---|---|---|---|---|
| Reference Example 13 | Br-benzothiazole-Me | m-F-phenyl-Me | 45.1 | 106 |
| Reference Example 14 | Me,Me-benzothiazole-Me | m-F-phenyl-Me | 31.6 | 222 |
| Reference Example 15 | Me-benzothiazole-Me | m-F-phenyl-Me | 27.9 | 260 |
| Reference Example 16 | MeO-benzothiazole-Me | m-F-phenyl-Me | 20.9 | 318 |
| Reference Example 17 | Cl-benzothiazole-Me | m-F-phenyl-Me | 33.8 | 204 |
| Reference Example 18 | F$_3$C-phenyl-Me | F-pyridine-Me | 1.8 | >1000 |

Reference Examples 1 to 12 are compounds in which the (N-alkylpyrrol-2-yl)-carbonyl group, which characterizes the compounds of the present invention, is replaced by another substituent such as a heterocyclic ring. As shown in Table 1, the piperazine compound having an (N-alkylpyrrol-2-yl)-carbonyl group as in the compounds of the present invention showed a strong H-PGDS inhibitory effect, whereas Reference Examples 1 to 12 showed little inhibitory effect.

Further, Reference Examples 13 to 17 are compounds having a structure similar to that of the compounds of the present invention, i.e., a structure comprising a fluorobenzoyl group and an aminocarbonyl group, and having a high GST2 inhibitory activity (Range A). Reference Example 18 is a compound comprising a fluoropyridinecarbonyl group and an aminocarbonyl group, and is effective against metabolic syndrome in mice. All of these compounds are disclosed in Patent Literature 3.

It is clear that the compounds of the present invention show a stronger H-PGDS inhibitory effect than Reference Examples 13 to 18.

Test Example 2

PGD2 Production Inhibiting Action in the Nasal Cavities of Guinea Pigs with Antigen-Induced Rhinitis A physiological saline solution containing 1 mg/mL of ovalbumin was subcutaneously injected into the back of 5-week-old male Std:Hartley guinea pigs in an amount of 1 mL/body for active sensitization (initial sensitization). One week and two weeks after initial sensitization, 20 μL of a physiological saline solution containing 10 mg/mL of ovalbumin was instilled into each nasal cavity using a micropipette (sensitization by nasal administration). Three weeks after initial sensitization, 20 μL of a physiological saline solution containing 10 mg/mL of ovalbumin was instilled into each nasal cavity using a micropipette to induce a rhinitis reaction.

The test compound (30 mg/kg) was orally administered 1 hour before induction of a rhinitis reaction. The animals in the control group only received the medium orally.

30 minutes after the induction of a rhinitis reaction, the nasal cavities were washed under pentobarbital sodium anesthesia. A nasal cavity washing liquid (phosphate buffered saline containing 3 mM of EDTA and 10 μM of indomethacin) was flushed using a Peristaltic Pump (Gilson, Inc.) in the direction from the trachea to the upper respiratory tract at the flow rate of 1 mL/min, and the liquid flowing out from the nasal cavities was collected for 1 minute. The collected liquid was centrifuged to separate the supernatant as the nasal cavity washing fluid. The concentration of PGD2 in the nasal cavity washing fluid was determined using an EIA kit (Prostaglandin D2-MOX EIA kit, Cayman Chemical).

The rate of decrease in PGD2 in the nasal cavity washing fluid was calculated by the following formula. Table 2 shows the results.

Rate of decrease in PGD2 in the nasal cavity washing fluid(%)={(PGD2 concentration in the control group−PGD2 concentration in the compound-administered group)÷(PGD2 concentration in the control group−PGD2 concentration in the normal group)}×100

8 or more cases were obtained from each group to determine whether expression of the PGD2 production inhibiting action occurred, and the PGD2 concentration in the nasal cavity washing fluid was compared between the control group and each compound-administered group. Note that when the significance level was below 0.05, the action was considered to be present and indicated by a symbol (*) in the table. Reference Example 19, known as an H-PGDS inhibitor, was used as a positive control substance.

TABLE 2

| Compound | Rate of decrease in PGD2 concentration in the nasal cavity washing fluid (%) |
| --- | --- |
| Example 3 | 77.5* |
| Reference Example 19 | 77.0* |
| Reference Example 13 | 7.9 |
| Reference Example 14 | 3.9 |
| Reference Example 15 | 26.6 |
| Reference Example 16 | −27.4 |
| Reference Example 17 | −38.1 |
| Reference Example 18 | 31.0 |

According to the results in Table 2, the compound of the present invention indicated a similar rate of decrease in the PGD2 concentration to that of Reference Example 19 (these compounds have the action). In contrast, Reference Examples 13 to 18 disclosed in Patent Literature 3 did not show a significant decrease in the PGD2 concentration.

Test Example 3

Eosinophil Infiltration Inhibiting Action in Guinea Pigs with Antigen-Induced Rhinitis A physiological saline solution containing 1 mg/mL of ovalbumin was subcutaneously injected into the back of 5-week-old male Std:Hartley guinea pigs in an amount of 1 mL/body for active sensitization (initial sensitization). One week and two weeks after initial sensitization, 20 μL of a physiological saline solution containing 10 mg/mL of ovalbumin was instilled into each nasal cavity using a micropipette (sensitization by nasal administration). Three weeks after initial sensitization, 20 μL of a physiological saline solution containing 10 mg/mL of ovalbumin was instilled into each nasal cavity using a micropipette to induce a rhinitis reaction.

The test compound (30 mg/kg) was orally administered 3 times in total (2 times at sensitization by nasal administrations and 1 time at the induction of a rhinitis reaction), 1 hour before sensitization or induction. The animals in the control group only received the medium orally.

6 hours after the induction of a rhinitis reaction, the nasal cavities were washed under pentobarbital sodium anesthesia. A nasal cavity washing liquid (phosphate buffered saline containing 3 mM of EDTA and 10 μM of indomethacin) was flushed using a Peristaltic Pump (Gilson, Inc.) in the direction from the trachea to the upper respiratory tract at the flow rate of 1 mL/min, and the liquid flowing out from the nasal cavities was collected for 3 minutes. The collected liquid was filtered through a cell strainer (40 μm), and centrifuged at 4° C., 300×g, for 10 minutes. Subsequently, the supernatant was removed by suction. 250 μL of nasal cavity washing liquid was added to the cell pellet to form a suspension. The total number of cells (×105 cells) in the cell suspension was determined using an automated blood cell counter (F-820, Sysmex Corporation).

A cell smear was prepared using a centrifugal device to collect cells (Cytospin-3, Shandon). After the cells were stained using a cell stain solution, the number of monocytes, the number of eosinophils, and the number of neutrophils were counted to obtain 300 cells in total by observation under a microscope (200-times magnification). The component ratio of each cell was calculated, and the number of eosinophils in the nasal cavity washing liquid was determined by the following formula.

Number of eosinophils($>10^5$ cells)=(Eosinophil count÷total count(300))×total number of cells The rate of decrease in the number of eosinophils in the nasal cavity washing liquid was regarded as the eosinophil infiltration inhibition rate, and determined by the following formula. Table 3 shows the results.

Inhibition rate(%)={(Number of eosinophils in the control group−number of eosinophils in the compound-administered group)÷(number of eosinophils in the control group−number of eosinophils in the normal group)}×100

16 cases were obtained from each group, and the number of eosinophils in the nasal cavity washing fluid was compared between the control group and each compound-administered group. Note that when the significance level was below 0.05, the eosinophil infiltration inhibiting action was considered to be present and indicated by a symbol (*) in the table.

TABLE 3

| Compound | Eosinophil infiltration inhibition rate (%) |
| --- | --- |
| Example 3 | 49.9* |
| Reference Example 13 | 34.2 |
| Reference Example 14 | −25.1 |
| Reference Example 15 | −133.3* |
| Reference Example 16 | −108.0* |
| Reference Example 17 | 16.6 |

The results in Table 3 clearly show that the compound of the present invention has a significant eosinophil infiltration inhibiting action. In contrast, Reference Examples 13 to 17 disclosed in Patent Literature 3 as the compounds having a high GST2 inhibitory activity (Range A) either increased eosinophil infiltration or did not show a significant eosinophil infiltration inhibiting action.

Test Example 4

Forelimb Grip Strength Test in Mice 4-week-old male C57BL/10-mdx (mdx) mice were used as a disease group, and 4-week-old male C57BL/10Sn (wild) mice were used as a normal group in the test. A acclimation period was provided after the arrival of the mice. An initial value of each individual was measured at 5 weeks of age, and 10 mice were assigned to each group. From the following day, the test compound (30 mg/kg) was orally administered to the mice once a day consecutively for 4 weeks. The animals in the control group only received the vehicle orally. The forelimb grip strength was measured at 4 weeks after the start of the administration. A value obtained by dividing the average of 5 forelimb grip strength measurement values (kg) determined using a small animal grip strength measurement device (GPM-100M, Melquest) by the body weight (kg) was used as the evaluation index (reference literature: Muscle Nerve., 35, 43-48 (2007)).

9 or more cases were obtained from each group to determine whether expression of forelimb grip strength enhancing action occurred. First, a significant decrease in the value of the control group compared to that of the normal group was confirmed, and then the value of the control group was compared with the value of the compound-administered group. When the significance level was below 0.05, the action was considered to be present and indicated by symbols (#) and (*) in the table. Table 4 shows the results.

TABLE 4

| Group | Forelimb grip strength measurement value/body weight (kg/kg) |
| --- | --- |
| Normal group | 5.40 ± 0.20 |
| Control group | 4.32 ± 0.17# |
| Example 3 | 4.80 ± 0.09* |
| Reference Example 13 | 4.37 ± 0.15 |
| Reference Example 14 | 4.26 ± 0.22 |
| Reference Example 15 | 4.20 ± 0.20 |
| Reference Example 16 | 4.29 ± 0.24 |
| Reference Example 17 | 4.48 ± 0.15 |

According to the results in Table 4, a significant decrease in the muscle strength was observed in the control group, compared with the normal group. It became evident that the compound of the present invention has an action of enhancing the forelimb grip strength, compared with the control group. In contrast, no significant enhancing action was observed in Reference Examples 13 to 17.

The invention claimed is:

1. A piperazine compound represented by Formula (I),

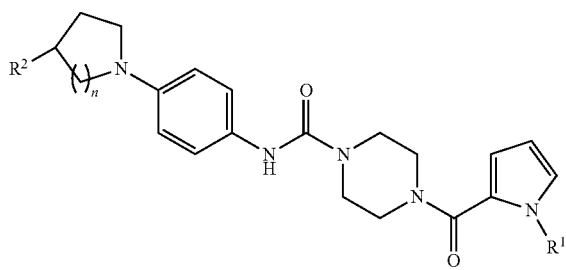

(I)

wherein
R$^1$ is C$_{1-6}$ alkyl;
R$^2$ is hydroxy, C$_{1-6}$ alkyl that may have one or more substituents, —(C=O)—N(R$^3$)(R$^4$), or —(C=O)—OR$^5$;
R$^3$ and R$^4$ are the same or different, and each represents hydrogen or C$_{1-6}$ alkyl that may have one or more substituents, or
R$^3$ and R$^4$, taken together with a nitrogen atom to which R$^3$ and R$^4$ are attached, form a saturated heterocyclic group;
R$^5$ is hydrogen or C$_{1-6}$ alkyl that may have one or more substituents; and
n is 1 or 2;
or a salt thereof;
further wherein said substituents are selected from the group consisting of halogen, hydroxy, cyano, nitro, alkyl, halogenoalkyl, cycloalkyl, cycloalkyl-alkyl, aralkyl, alkenyl, alkynyl, alkoxy, halogenoalkoxy, cycloalkoxy, cycloalkyl-alkoxy, aralkyloxy, alkylthio, cycloalkyl-alkylthio, amino, mono- or di-alkylamino, cycloalkyl-alkylamino, acyl, acyloxy, oxo, carboxy, alkoxycarbonyl, aralkyloxycarbonyl, carbamoyl, saturated or unsaturated heterocyclic groups, aromatic hydrocarbon, and saturated heterocycloxy groups; and
wherein the carbamoyl is selected from the group consisting of CONH$_2$, (mono- or di-alkyl)carbamoyl, (mono- or di-aryl)carbamoyl, (N-alkyl-N-aryl)carbamoyl, pyrrolidinocarbamoyl, piperidinocarbamoyl, piperazinocarbaomyl, and morpholinocarbamoyl.

2. The piperazine compound or salt thereof according to claim 1, wherein
R$^1$ is methyl or ethyl;
R$^2$ is hydroxy, C$_{1-6}$ alkyl that may have one or more saturated or unsaturated heterocyclic groups as substituents, —(C=O)—N(R$^3$)(R$^4$), or —(C=O)—OR$^5$;
R$^3$ and R$^4$ are the same or different, and each represents hydrogen or C$_{1-6}$ alkyl that may have one or more saturated or unsaturated heterocyclic groups as substituents, or
R$^3$ and R$^4$, taken together with a nitrogen atom to which R$^3$ and R$^4$ are attached, may form pyrrolidinyl, piperidinyl, piperazinyl, and morpholino;
R$^5$ represents hydrogen, methyl, ethyl, tert-butyl, or benzyl; and
n is 1 or 2.

3. The piperazine compound or salt thereof according to claim 1, wherein
R$^1$ is methyl;
R$^2$ is C$_{1-3}$ alkyl that may have morpholino or an unsaturated heterocyclic croup as a substituent, —(C=O)—N(R$^3$)(R$^4$), or —(C=O)—OR$^5$; wherein the unsaturated heterocyclic croup is a pyrazolyl or a triazolyl;
R$^3$ and R$^4$, taken together with a nitrogen atom to which R$^3$ and R$^4$ are attached, form morpholino;
R$^5$ represents hydrogen, methyl, or ethyl; and
n is 2.

4. The piperazine compound or salt thereof according to claim 1, wherein
R$^1$ is methyl;
R$^2$ is C$_{1-3}$ alkyl that may have morpholino or an unsaturated heterocyclic group as a substituent, —(C=O)—N(R$^3$)(R$^4$), or —(C=O)—OR$^5$; wherein the unsaturated heterocyclic group is 1,2,3-triazolyl or 1,2,4-triazolyl;
R$^3$ and R$^4$, taken together with a nitrogen atom to which R$^3$ and R$^4$ are attached, form morpholino;
R$^5$ represents hydrogen or ethyl; and
n is 2.

5. A piperazine compound or salt thereof selected from the group consisting of:
N-(4-(4-hydroxypiperidin-1-yl)-phenyl)-4-((1-methylpyrrol-2-yl)-carbonyl)-1-piperazinecarboxamide,
4-((((1-methylpyrrol-2-yl)-carbonyl)-1-piperazinyl)-carbonyl)amino-4-phenylpiperidine-4-carboxylic acid,
4-((1-methylpyrrol-2-yl)-carbonyl)-N-(4-(4-morpholin-1-yl-carbonylpiperidin-1-yl)-phenyl)-1-piperazinecarboxamide,
4-((1-methylpyrrol-2-yl)-carbonyl)-N-(4-(4-morpholinomethylpiperidin-1-yl)-phenyl)-1-piperazinecarboxamide,
4-((1-methylpyrrol-2-yl)-carbonyl)-N-(4-(3-(2-(1,2,4-triazole-1-yl)-ethyl)pyrrolidin-1-yl)-phenyl)-1-piperazinecarboxamide,
4-((1-methylpyrrol-2-yl)-carbonyl)-N-(4-(4-morpholinoethylpiperidin-1-yl)-phenyl)-1-piperazinecarboxamide,
4-((1-methylpyrrol-2-yl)-carbonyl)-N-(4-(4-(2-(1,2,3-triazol-1-yl)-ethyl)piperidin-1-yl)-phenyl)-1-piperazinecarboxamide, 4-((1-methylpyrrol-2-yl)-carbonyl)-N-(4-(4-(2-(1,2,4-triazol-1-yl)-ethyl)piperidin-1-yl)-phenyl)-1-piperazinecarboxamide, 4-((1-methylpyrrol-2-yl)-carbonyl)-N-(4-(4-(2-(3,5-dimethyl-1,2,4-triazol-1-yl)-ethyl)piperidin-1-yl)-phenyl)-1-piperazinecarboxamide, 4-((1-methylpyrrol-2-yl)-carbonyl)-N-(4-(4-(2-(pyrazol-1-yl)-ethyl)piperidin-1-yl)-phenyl)-1-piperazinecarboxamide, 4-((1-methylpyrrol-2-yl)-carbonyl)-N-(4-(4-(3-(1,2,4-triazol-1-yl)-propyl)piperidin-1-yl)-phenyl)-1-piperazinecarboxamide, 4-((1-methylpyrrol-2-yl)-carbonyl)-N-(4-(4-(3-(1,2,3-triazol-1-yl)-propyl)piperidin-1-yl)-phenyl)-1-piperazinecarboxamide, 4-((1-ethylpyrrol-2-yl)-carbonyl)-N-(4-(4-morpholin-1-yl-carbonylpiperidin-1-yl)-phenyl)-1-piperazinecarboxamide, 4-((1-methylpyrrol-2-yl)-carbonyl)-N-(4-(4-piperidin-1-yl-carbonylpiperidin-1-yl)-phenyl)-1-piperazinecarboxamide, 4-((1-methylpyrrol-2-yl)-carbonyl)-N-(4-(4-(4-methylpiperazin-1-yl-carbonyl)piperidin-1-yl)-phenyl)-1-piperazinecarboxamide, 4-((1-methylpyrrol-2-yl)-carbonyl)-N-(4-(4-(2-morpholinoethylcarbamoyl)piperidin-1-yl)-phenyl)-1-piperazinecarboxamide, and 4-((1-methylpyrrol-2-yl)-carbonyl)-N-(4-(4-(pyridin-3-ylmethylcarbamoyl)piperidin-1-yl)-phenyl)-1-piperazinecarboxamide.

6. A pharmaceutical composition comprising an effective amount of at least one of the compounds according to claim 1 or pharmaceutically acceptable salt thereof, and a pharmaceutically acceptable carrier.

* * * * *